(12) United States Patent
Sõritski et al.

(10) Patent No.: US 11,193,940 B2
(45) Date of Patent: Dec. 7, 2021

(54) MOLECULARLY IMPRINTED POLYMER SENSORS FOR NEUROTROPHIC FACTORS

(71) Applicant: TALLINN UNIVERSITY OF TECHNOLOGY, Tallinn (EE)

(72) Inventors: Vitali Sõritski, Tallinn (EE); Jekaterina Reut, Tallinn (EE); Anna Kidakova, Tallinn (EE); Andres Öpik, Tallinn (EE)

(73) Assignee: TALLINN UNIVERSITY OF TECHNOLOGY, Tallinn (EE)

( * ) Notice: Subject to any disclaimer, the term of this patent is extended or adjusted under 35 U.S.C. 154(b) by 422 days.

(21) Appl. No.: 16/377,414

(22) Filed: Apr. 8, 2019

(65) Prior Publication Data
US 2020/0319202 A1     Oct. 8, 2020

(51) Int. Cl.
*G01N 33/68* (2006.01)

(52) U.S. Cl.
CPC ... *G01N 33/6872* (2013.01); *G01N 2333/475* (2013.01); *G01N 2600/00* (2013.01)

(58) Field of Classification Search
CPC ......... G01N 33/6872; G01N 2333/475; G01N 2600/00; G01N 2333/48; G01N 33/6896; G01N 33/543
See application file for complete search history.

(56) References Cited

U.S. PATENT DOCUMENTS

2004/0126814 A1* 7/2004 Singh ........................ C08F 8/00
                                                                  435/7.1
2007/0134721 A1   6/2007 Laitenberger et al.

FOREIGN PATENT DOCUMENTS

WO    WO 2018/162611        9/2018

OTHER PUBLICATIONS

Boroznjak, R. et al. "A computational approach to study functional monomer-protein molecular interactions to optimize protein molecular imprinting" *Journal of Molecular Recognition*, 2017, pp. 1-9, e2635.
Cardoso, A. R. et al. "In-situ generated molecularly imprinted material for chloramphenicol electrochemical sensing in waters down to the nanomolar level" *Sensors and Actuators B: Chemical*, 2018, pp. 420-428, vol. 256.
Diaz-Diaz, G. et al. "Preparation and Characterization of a Molecularly Imprinted Microgel for Electrochemical Sensing of 2,4,6-Trichlorophenol" *Electroanalysis*, 2011, pp. 201-208, vol. 23, No. 1.

(Continued)

*Primary Examiner* — Jennifer Wecker
*Assistant Examiner* — Michael Paul Shimek
(74) *Attorney, Agent, or Firm* — Saliwanchik, Lloyd & Eisenschenk

(57) ABSTRACT

The present invention relates to a sensor for the detection of Neurotrophic Factor (NF). The sensor, preferably a Screen Printed Electrochemical sensor (SPE), has a working electrode coated by a Molecularly Imprinted Polymer (MIP) imprinted by a NF. The invention also relates to a method for preparing such a sensor and comprising the steps of 1) formation of a cleavable linking layer on the working electrode of the sensor; 2) immobilization of NF molecules on the cleavable linking layer; 3) polymerization of m-PD on the working electrode of the sensor; and 4) cleavage of the cleavable linking layer thereby removing the NF molecules from the MIP layer.

19 Claims, 7 Drawing Sheets

(56) References Cited

OTHER PUBLICATIONS

Ekomo, V. M. et al. "Detection of Bisphenol A in aqueous medium by screen printed carbon electrodes incorporating electrochemical molecularly imprinted polymers" *Biosensors and Bioelectronics*, 2018, pp. 156-161, vol. 112.

Hayat, A. et al. "Disposable Screen Printed Electrochemical Sensors: Tools for Environmental Monitoring" *Sensors*, 2014, pp. 10432-10453, vol. 14.

Kidakova, A. et al. "Electrochemical detection of brain-derived neurotrophic factor by molecularly-imprinted polymer on screen-printed electrode" *The 10th International Conference on Molecular Imprinting MIP* 2018, Jerusalem, Israel, Jun. 24-28, 2018, Poster, p. 1, retrieved from Internet: https://events.eventact.com/ProgramView2/Agenda/Lecture?id=175959&code=3635110.

Kidakova, A. et al. "Electrochemical detection of brain-derived neurotrophic factor by molecularly-imprinted polymer on screen-printed electrode" *The 10th International Conference on Molecular Imprinting MIP* 2018, Jerusalem, Israel, Jun. 24-28, 2018, Abstract, pp. 1-2.

Knaepen, K. et al. "Neuroplasticity—Exercise-Induced Response of Peripheral Brain-Derived Neurotrophic Factor; A Systematic Review of Experimental Studies in Human Subjects" *Sports Medicine*, 2010, pp. 765-801, vol. 40, No. 9.

Laske, C. et al. "Stage-dependent BDNF serum concentrations in Alzheimer's disease" *Journal of Neural Transmission*, 2006, pp. 1217-1124, vol. 113.

Lopes, F. et al. "Molecularly imprinted electrochemical sensor prepared on a screen printed carbon electrode for naloxone detection" *Sensors and Actuators B: Chemical*, 2017, pp. 745-752, vol. 243.

Ribeiro, J. A. et al. "Electrochemical detection of cardiac biomarker myoglobin using polyphenol as imprinted polymer receptor" *Analytica Chimica Acta*, 2017, pp. 41-52, vol. 981.

Sen, S. et al. "Serum Brain-Derived Neurotrophic Factor, Depression, and Antidepressant Medications: Meta-Analyses and Implications" *Biol Psychiatry*, 2008, pp. 527-532, vol. 64.

Shumyantseva, V. V. et al. "Electroanalysis of Myoglobin Based on Electropolymerized Molecularly Imprinted Polymer Poly-o-Phenylenediamme and Carbon Nanotubes/Screen Printed Electrode" *Biochemistry, Biophysics and Molecular Biology*, 2016, pp. 213-216, vol. 468.

Tretjakov, A. et al. "Surface molecularly imprinted polydopamine films for recognition of immunoglobulin G" *Microchim Acta*, 2013, pp. 1433-1442, vol. 180.

Wang, Y. et al. "Low BDNF is associated with cognitive impairments in patients with Parkinson's disease" *Parkinsonism and Related Disorders*, 2016, pp. 66-71, vol. 29.

Yazdani, Z. et al. "A molecularly imprinted electrochemical nanobiosensor for prostate specific antigen determination" *Analytical Biochemistry*, 2019, pp. 116-125, vol. 566.

\* cited by examiner

MOLECULARLY IMPRINTED POLYMER SENSORS FOR NEUROTROPHIC FACTORS

FIELD OF THE INVENTION

The present invention relates to the field of sensors and more particularly to sensors for medical diagnosis. The present invention relates to a sensor coated by a Molecularly Imprinted Polymer specific for a Neurotrophic Factor.

BACKGROUND OF THE INVENTION

Nowadays, the heart of the healthcare system is clinical diagnostics, i.e. the detection of biomarkers of human diseases. There is a constant need for new biomarkers with improved sensitivity or selectivity, new biomarkers able to diagnose the disease at an early stage or even to prognostic it. This is especially true with neurological and mental disorders since developed countries are facing a dramatic increase of the prevalence of these diseases over the last decades.

Neurotrophic factors (NFs) are a family of biomolecules that plays a major role in the development, function, and/or survival of a variety of cell types, and in particular neurons. A number of NFs have been identified so far, including the members of the neurotrophin family that comprises the Nerve Growth Factor (NGF), the Neurotrophin-3 (NT-3), the Neurotrophin-4/5 (NT-4/5), the Neurotrophin-6 (NT-6) and the Brain Derived Neurotrophic Factor (BDNF).

The death or dysfunction of neurons have been directly implicated in several neurological disorders such as Alzheimer's, Parkinson's, Huntington's disease, Rett syndrome and amyotrophic lateral sclerosis (ALS), among others. It has been suggested that alterations in NFs localization, in their expression levels, and/or in the expression levels of their receptors can trigger neuronal degeneration as well as neuron dysfunctions. For example, BDNF has been associated with Alzheimer's (Laske et al, Journal of Neural Transmission, 2006, 113(9): pp. 1217-1224) and Parkinson's (Wang et al, Parkinson & Related Disorders, 2016, 29: pp. 66-71) neurodegenerative disorders. NFs also mediate fundamental mechanisms relevant to other disorders including for example depression, obesity, and ischemic conditions of peripheral tissues. For example, BDNF has been associated with depression (Sen et al, Biological Psychiatry, 2008, 64(6): pp. 527-532). NFs, and especially BDNF, are thus considered as new important biomarkers for various conditions affecting the brain function.

A wide variety of powerful analytical techniques already exist to detect molecules such as NFs, for example immunoassays methods and chromatographic techniques. These techniques are able to perform very accurate analysis. However, they are time consuming and require bulky equipment, they also involve high costs and require highly trained personnel. These techniques are also not portable. Moreover, concerning immunoassay, e.g. in ELISA, one of the key challenges is the requirement for labeling that can potentially alter intrinsic properties of biomolecules and consequently the accuracy of the measurements.

There is thus still an increasing demand nowadays for new NF sensors, such as BDNF sensors, capable to detect specific NFs in a fast, simple, low-cost, reliable, portable, selective and sensitive way. The present invention meets these and other needs.

SUMMARY OF THE INVENTION

In search for a miniaturized, portable, simple, cost-effective and sensitive NF sensor, the inventors tried to combine electrochemical sensor technology with Molecularly Imprinted Polymer technology (MIP). To that end, the inventors successfully developed a Screen-Printed Electrochemical sensor (SPE) in which a BDNF specific MIP is coating the working electrode of the SPE.

The inventors developed a sensor with excellent detection abilities in the range of about 0.06 ng/ml to about 0.2 ng/ml with a Limit of Detection (LOD) of about 0.04 ng/ml and a Limit Quantitation of about 0.12 ng/ml. These ranges are perfectly adapted to the detection of BDNF level in the serum of patients which typical values ranging from 1.5 to 30.9 ng/mL according to literature (Knaepen K et al, Sports medicine, 2010, 40 (9), pp. 765-801). The sensor obtained is also selective of BDNF with respect to interfering proteins.

Thus, in a first aspect, the invention relates to a MIP layer coated electrically conductive surface, wherein said MIP layer comprises a m-phenylenediamine (m-PD) polymer and Neurotrophic Factor (NF) imprints.

In a preferred embodiment, the thickness of the MIP layer according to the invention is between about 3.5 and about 7 nm, preferably the thickness of the MIP layer is of about 4.7 nm.

In another preferred embodiment, the electrically conductive surface comprises a metal, preferably selected from ruthenium, rhodium, palladium, silver, osmium, iridium, platinum, gold, and a mixture thereof, more preferably the electrically conductive surface comprises gold.

In a second aspect, the invention also relates to a method for preparing a MIP layer coated electrically conductive surface, wherein the MIP layer comprises a m-PD polymer and NF imprints, and wherein the method comprises the following steps:

1) formation of a cleavable linking layer on the electrically conductive surface;
2) immobilization of NF molecules on the cleavable linking layer;
3) polymerization of m-PD on the NF-immobilized electrically conductive surface thereby forming a polymeric layer coating said electrically conductive surface with entrapped NF; and
4) cleavage of the cleavable linking layer thereby removing the NF molecules from the polymeric layer and obtaining the MIP layer.

Preferably, the thickness of the MIP layer and the electrically conductive surface are as above described.

In a particular embodiment, the electrically conductive surface according to the invention is cleaned prior to step 1, preferably the electrically conductive surface is electrochemically cleaned.

The above described step of formation of a cleavable linking layer may comprise:

1) the formation of a 4-aminothiophenol (4-ATP) monolayer on the electrically conductive surface; and
2) the formation of a 3,3'-dithiobis(sulfosuccinimidyl propionate) (DTSSP) monolayer covalently linked to the 4-ATP monolayer.

The above described step of immobilization of NF molecules on the cleavable linking layer may comprise the immersion of the electrically conductive surface in a solution comprising between about 20 µg/ml and about 30 µg/ml, preferably about 25 µg/ml of NF.

The above described step of polymerization of m-PD is preferably an electropolymerization, and preferably comprises the steps of:

immersing the NF-immobilized electrically conductive surface in a solution comprising about 10 mM of m-PD; and applying to said NF-immobilized electrically conductive surface a constant potential of about 0.26 V until an electric charge of about 2 mC/cm$^2$ has been passed through the NF-immobilized electrically conductive surface.

The above described step of cleaving the cleavable linking layer may comprise the immersion of the polymeric layer in an ethanolic solution comprising about 0.1 M of 2-mercaptoethanol for about 7 h to about 15 h followed by the immersion of the polymeric layer in an acetic acid aqueous solution concentrated at about 10% for about 30 minutes.

The method for preparing a MIP layer coated electrically conductive surface according to the invention may further comprise after step 4, a step of washing the MIP layer coated electrically conductive surface, preferably with water, more preferably with ultra-pure water.

The method for preparing a MIP layer coated electrically conductive surface according to the invention may further comprise after step 4 or after the washing step, a step of drying the MIP layer coated electrically conductive surface, preferably under a nitrogen flow.

In a third aspect, the invention also relates to a MIP layer coated electrically conductive surface directly obtained by the method for preparing a MIP layer coated electrically conductive surface according to the invention.

In a fourth aspect, the invention relates to a NF Sensor comprising at least one MIP layer coated electrically conductive surface according to the invention.

In a preferred embodiment, the NF sensor is a Screen Printed Electrochemical sensor (SPE) and the at least one MIP layer coated electrically conductive surface is an electrically conductive surface of the working electrode of said SPE.

In a particular embodiment, the NF sensor has a limit of detection (LOD) of about 0.04 ng/ml and a limit of quantitation (LOQ) of about 0.12 ng/ml.

In a fifth aspect, the invention relates the use of a NF sensor according to the invention for detecting and/or measuring the concentration of a NF in a liquid medium.

In a sixth aspect, the invention further relates to an in-vitro method of detection of a NF in a liquid medium or of measuring the concentration of a NF in a liquid medium, the method comprising contacting a NF sensor according to the invention with said liquid medium.

The liquid medium according to the invention is preferably a sample from a patient, more preferably selected from blood samples, plasma samples, serum samples, lymph samples, urine samples, saliva samples, or cerebrospinal fluid samples from a patient, even more preferably the liquid medium is a serum sample from a patient.

In a seventh aspect, the invention also relates to an in-vitro diagnosis method, prognosis method or method for assessing the effectiveness of a treatment of a disorder selected from neurological disorders, mental disorders, neurodegeneration disorders, and metabolic disorders such as depressive disorders, Alzheimer's disease, Parkinson's disease, Huntington's disease, and amyotrophic lateral sclerosis in a patient in need thereof, wherein the presence or concentration of a NF is detected or measured in a sample from said patient according to the in-vitro method of detection of a NF or of measuring the concentration of a NF according to the invention.

Preferably, the patient according to the invention is a mammal, more preferably a human.

In a preferred embodiment, the NF according to the invention is a neurotrophin, preferably selected from the Brain Derived Neurotrophic Factor (BDNF), the Nerve Growth Factor (NGF), the neurotrophin 3 (NT3), the neurotrophin 4 (NT4), and variants or combinations thereof, more preferably the NF is the BDNF.

In another preferred embodiment, the NF is a human NF, preferably a human neurotrophin, more preferably the human BDNF.

DETAILED DESCRIPTION OF THE INVENTION

Figure 1:
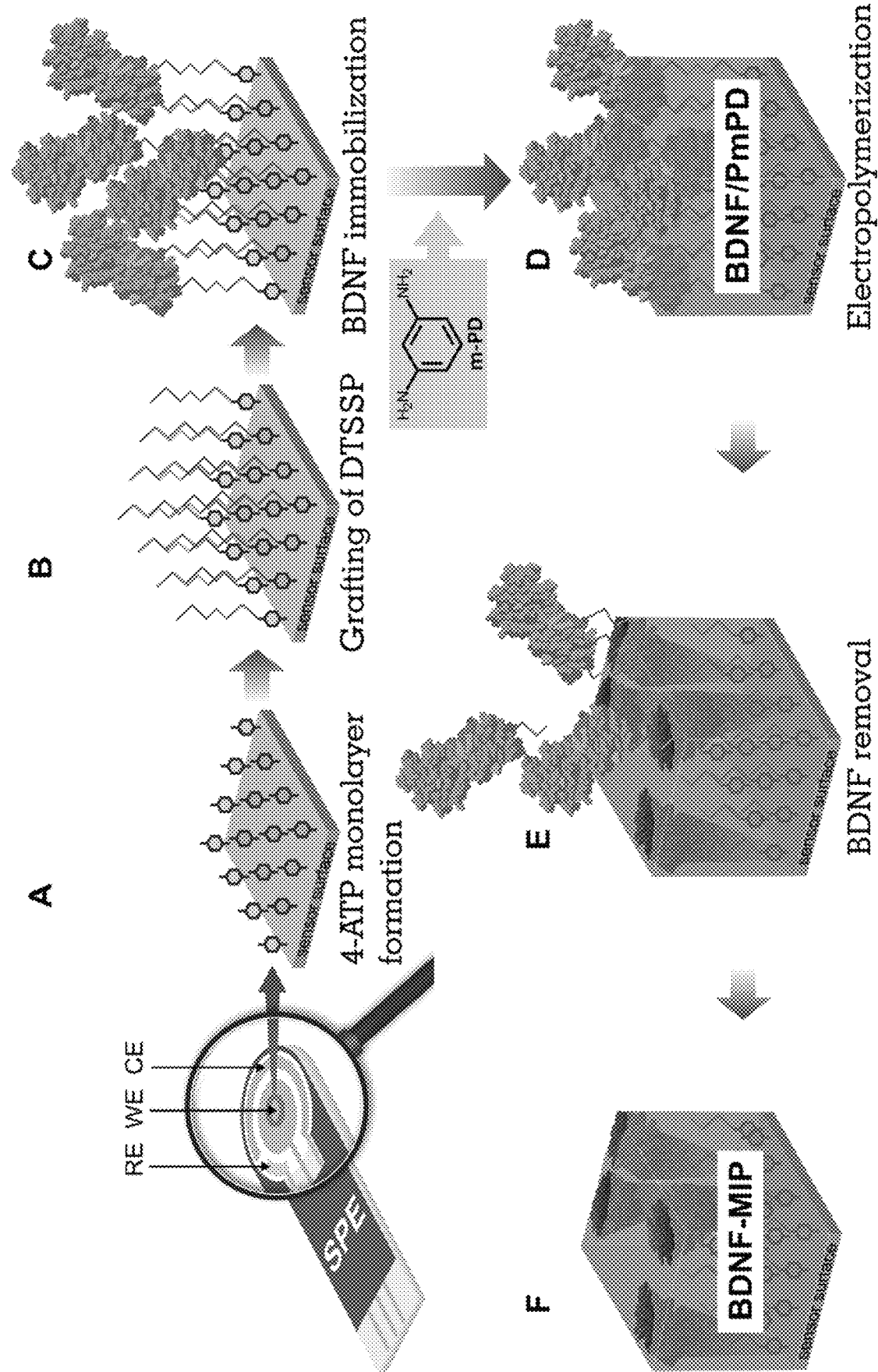
FIG. 1: Scheme of the strategy for coating the working electrode of a SPE by a BDNF-MIP layer; BDNF is used as the template and m-phenylenediamine (m-PD) as a functional monomer: a) functionalization of a Working Electrode with amino groups by self-assembly of 4-ATP layer; b) grafting of the DTSSP cleavable linker; c) BDNF immobilization by covalent attachment to the DTSSP linker; d) electropolymerization of m-PD resulting in a BDNF-Pm-PD film; e) BDNF removal by cleavage of linker and subsequent treatment in an acidic solution; f) BDNF-MIP film is formed.

The inventors have developed a NF sensor combining an electrochemical sensor with a NF specific MIP. More specifically, the inventors have produced a SPE sensor in which a BDNF specific MIP is coating the working electrode of the SPE. To our knowledge, this is the first time that the MIP technology is used to imprint BDNF, or to imprint any NF. The size of the BDNF molecule was particularly challenging as a thin MIP is recommended to allow efficient transduction of the signal to the SPE. The BDNF sensor of the invention is not only miniaturized, portable, simple, and cost-effective, it is also a very sensitive, specific and selective for BDNF, making it of prime interest in the field of medical diagnostics.

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

The terms "a", "an", and "the" refer to "one or more" when used in this application, including the claims. Thus, for example, reference to "a neurotrophic factor" includes mixtures of one or more neurotrophic factors, two or more neurotrophic factors, and the like.

Unless otherwise indicated, all numbers expressing quantities of ingredients, reaction conditions, and so forth used in the specification and claims are to be understood as being modified in all instances by the term "about". As used herein, the term "about" when referring to a measurable value such as an amount of weight, time, dose, etc. is meant to encompass in one example variations of ±20%, preferably ±10%, more preferably ±5%, alternatively ±2%, still alternatively ±1% and yet alternatively ±0.1% from the specified amount. For example, "about 20" include all the values ranging from ±5% of 20, i.e. a range of values from 19 to 21.

In a first aspect, the invention relates to a Molecularly Imprinted Polymer (MIP) layer imprinted with a neurotrophic factor (NF).

As used herein the term "Molecularly Imprinted Polymer" or "MIP" refers to functional monomers polymerized in the presence of a template molecule to form a cast-like shell. The template molecules, i.e. neurotrophic factors in the present invention, are to be removed after polymerization. At the end of the process, the MIP contains binding sites, the imprints, which are complementary to the target molecules, i.e. the neurotrophic factors described in the present invention, with respect to size, shape, position of functional groups, and which are kept in place by the polymer matrix. Substantially, a molecular memory, that can selectively bind targets, is imprinted in the polymer (K. Haupt, Nature Materials, 9 (2010) 612-614). The robust nature of MIP, the ease and low cost of its fabrication on sensor surfaces make it an ideal recognition layer for combining with electrochemical sensors.

As used herein, the term "Molecularly Imprinted Polymer Layer" or "MIP layer" refers to a layer comprising polymerized m-phenylenediamine (m-PD). In a preferred embodiment, the MIP layer is essentially constituted of polymerized m-PD (Poly-m-PD).

As used herein, the terms "m-phenylenediamine", "m-PD", "1,3-diaminobenzene", and "Benzene-1,3-diamine" are equivalent and refer to an organic compound with the formula $C_6H_4(NH_2)_2$ and the following chemical structure:

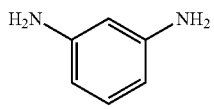

m-phenylenediamine must be distinguished from o-phenylenediamine and p-phenylenediamine which are its isomers.

The MIP layer may comprise other molecules, for examples additives, co-polymers, solvents, or linking molecules or parts of linking molecules. Linking molecules may be used to trap the NF in the Poly-m-PD layer while polymerizing as described in the fifth aspect of the invention below.

Preferably, the MIP layer is essentially constituted of Poly-m-PD, which means that at least about 70%, preferably at least about 80%, more preferably at least about 90%, still preferably at least about 95%, even more preferably at least about 99% of its composition in mass is Poly-m-PD.

In a most preferred embodiment, the MIP layer is constituted of Poly-m-PD and cleaved linking molecules, preferably sulfosuccinimidyl 1-thiopropionate, the cleaved linking molecules constituting less than about 15%, preferably less than about 10%, more preferably less than about 5%, still preferably less than about 1%, even more preferably less than about 0.1% in mass of the MIP layer.

The MIP layer according to the invention is imprinted by a Neurotrophic Factor (NF). As used herein the term "Neurotrophic Factor" or "NF" refers to a family of biomolecules, nearly all of which are peptides or small proteins, that support the growth, survival, and differentiation of developing and/or mature neurons. Most NFs exert their trophic effects on neurons by signaling through tyrosine kinases, usually a receptor tyrosine kinase. In the mature nervous system, they promote neuronal survival, induce synaptic plasticity, and modulate the formation of long-term memories. NFs also promote the initial growth and development of neurons in the central nervous system and peripheral nervous system. Some NFs are also released by the target tissue in order to guide the growth of developing axons. According to the invention, the term "neurotrophic factor" encompasses all neurotrophins, growth factors, and other substances that promote survival and repair of the cells of the nervous system.

Thus, the NF according to the invention can be selected from various members of the neurotrophin family such as Nerve growth factor (NGF), Brain-derived neurotrophic factor (BDNF), neurotrophin 3 (NT-3), neurotrophin 4/5 (NT-4/5), neurotrophin 6 (NT-6), or neurotrophin 7 (NT-7); the neuropoietic cytokines or neurokines such as members of the Ciliary neurotrophic factor (CNTF) family, Leukemia inhibitory factor (LIF), cholinergic differentiation factor, cardiotrophin-1, oncostatin M, growth promoter activity factor, tumor necrosis factor (TNF), interleukin-6 (IL-6), prolactin, growth hormone (GH), leptin, interferon-α, interferon-β, and interferon-γ; Epidermal Growth factor (EGF) and Transforming Growth Factor (TGF) families such as of EGF, p185erbB2, p160erbB3, p180erbB4, neuregulin family including neu differentiation factor or heregulin, acetylcholine receptor-inducing activity, and Glial growth factors (GGFs), TGFα, TGFβ, Glial cell line-derived neurotrophic factor (GDNF), artemin, neurturin, persephin, osteogenic protein-1 (OP-1), bone morphogenetic proteins (BMPs), and growth differentiation factors; Fibroblast growth factor (FGF) family; Insulin-like growth factor (IGF) family; platelet-derived growth factor (PDGF) family; Hepatocyte growth factor (HGF) family; granulocyte-colony stimulating factor (G-CSF) family; neuroimmunophilins; pigment epithelium-derived factor (PEDF) family; activity-dependent neurotrophic factors such as activity-dependent neuroprotective protein (ADNP) and neuritin (activity-induced neurotrophic factor); angiogenesis growth factor family; vascular endothelial growth factor (VEGF) family; cerebral dopamine neurotrophic factor (CDNF) family; mesencephalic astrocyte-derived neurotrophic factor (MANF) family; Ephrins family such as ephrin A1, ephrin A2, ephrin A3, ephrin A4, ephrin A5, ephrin B1, ephrin B2, and ephrin B3; DHEA; glia maturation factor; insulin; pituitary adenylate cyclase-activating peptide (PACAP); interleukin-1 (IL-1); interleukin-2 (IL-2); interleukin-3 (IL-3); interleukin-5 (IL-5); interleukin-8 (IL-8); macrophage colony-stimulating factor (M-CSF); granulocyte-macrophage colony-stimulating factor (GM-CSF); neurotactin; neurotransmitters and neuromodulators; serine protease inhibitors such as protease nexin-1, hedgehog family of inducing proteins; proteins involved in synapse formation such as agrin, laminin 2, and ARIA (ACh-inducing activity); variants and combinations thereof.

In a preferred embodiment, the NF according to the invention is a neurotrophin, preferably a neurotrophin selected from Nerve growth factor (NGF), Brain-derived neurotrophic factor (BDNF), neurotrophin 3 (NT-3), neurotrophin 4/5 (NT-4/5), neurotrophin 6 (NT-6), neurotrophin 7 (NT-7), variants and combination thereof; more preferably the neurotrophin is selected from Nerve growth factor (NGF), Brain-derived neurotrophic factor (BDNF), neurotrophin 3 (NT-3), neurotrophin 4/5 (NT-4/5), variants and combinations thereof.

In a most preferred embodiment, the NF according to the invention is the Brain-derived neurotrophic factor (BDNF) or a variant thereof. BDNF (UniProt KB: P23560) plays an important role in neuronal survival and growth, serves as a neurotransmitter modulator, and participates in neuronal plasticity, which is essential for learning and memory. It is widely expressed in the Central Nervous System, gut and other tissues. BDNF binds to its high affinity receptor TrkB (tyrosine kinase B) and activates signal transduction cascades (IRS1/2, PI3K, Akt), crucial for CREB and CBP production, that encode proteins involved in β cell survival. BDNF regulates glucose and energy metabolism and prevents exhaustion of β cells. Decreased levels of BDNF have been associated with neurodegenerative diseases with neuronal loss, such as Parkinson's disease, Alzheimer's disease, multiple sclerosis and Huntington's disease (Laske et al, Journal of Neural Transmission, 2006, 113(9): pp. 1217-1224; Wang et al, Parkinson & Related Disorders, 2016, 29: pp. 66-71). BDNF is also associated with several other diseases including diabetes mellitus.

In a particular embodiment, the NF according to the invention is a combination of 2, 3, 4, 5, 6, 7, 8, 9, 10, 11, 12, 13, 14, 15, 16, 17, 18, 19, or 20 NFs, preferably a combination of 2, 3, 4, 5 or 6 neurotrophins selected from Nerve growth factor (NGF), Brain-derived neurotrophic factor (BDNF), neurotrophin 3 (NT-3), neurotrophin 4/5 (NT-4/5), neurotrophin 6 (NT-6), neurotrophin 7 (NT-7), and variants thereof, more preferably a combination of 2, 3, or 4 neurotrophins selected from Nerve growth factor (NGF), Brain-derived neurotrophic factor (BDNF), neurotrophin 3 (NT-3), neurotrophin 4/5 (NT-4/5), and variants thereof. In case of a combination of NFs imprinting the MIP, each NF of the combination may account for 1% to 99% of the imprints, providing that the total of the percentages of all the imprint types is equal to 100%. For example, in a MIP layer imprinted by the Nerve growth factor (NGF), Brain-derived neurotrophic factor (BDNF), neurotrophin 3 (NT-3), and neurotrophin 4/5 (NT-4/5), each neurotrophin may account for 25% of the imprints.

In a preferred embodiment, the NF according to the invention is a mammal NF, more preferably a mammal neurotrophin, even more preferably a mammal neurotrophin selected from NGF, BDNF, NT-3, NT-4/5, and variants thereof, still preferably a mammal BDNF or a variant thereof. The mammal according to the invention can be selected from cattle, goat, sheep, horse, pig, cat, dog, rabbit, mouse, rat, guinea-pig, zebu, donkey, buffalo, camel, lama yak, alpaca, ferret, reindeer, deer, moose, elephant, squirrel, elk, mink, hamster, chinchilla, bison, gerbil, monkey, primate and human. In a most preferred embodiment, the mammal is a human.

In another embodiment, the NF according to the invention is a bird NF, preferably selected from parrot, fowl, and poultry such as turkeys, chickens, ducks, geese, guinea fowl.

In a most preferred embodiment, the NF according to the invention is a human NF, more preferably a human neurotrophin, even more preferably a human neurotrophin selected from NGF, BDNF, NT-3, NT-4/5, and variants thereof, still preferably a human BDNF or a variant thereof.

The MIP layer according to the invention has a certain thickness, size and shape.

In a preferred embodiment, the MIP layer according to the invention has a thickness between about 1 and about 50 nm, preferably between about 2 and about 25 nm, more preferably between about 3 and about 10 nm, even more preferably between about 3.5 and about 7 nm. In a most preferred embodiment, the thickness of the MIP layer according to the invention is of about 4.7 nm.

In another preferred embodiment, the MIP layer according to the invention has a size between about 1 nm$^2$ and about 10 cm$^2$, preferably between about 1 μm$^2$ and about 1 cm$^2$, more preferably between about 10 μm$^2$ and about 100 mm$^2$, even more preferably between about 0.1 mm$^2$ and 10 mm$^2$. In a most preferred embodiment, the size of the electrically conductive surface according to the invention is of about 0.80 mm$^2$.

The MIP layer according to the invention can be of any shape. Preferably, it has a rectangular, square or circular shape, more preferably a circular shape.

In a second aspect, the invention also relates to a MIP layer coated electrically conductive surface, said MIP layer comprising a m-phenylenediamine (m-PD) polymer and Neurotrophic Factor (NF) imprints.

The Neurotrophic Factor, the MIP layer and the m-PD are as described in the first aspect above mentioned.

As used herein, the term "MIP layer coated electrically conductive surface" refers to an electrically conductive surface at least partially coated by a MIP layer. As used herein the terms "electrically conductive surface" and "conductor surface" are equivalent and refer to a surface that allows the flow of an electrical current.

The electrically conductive surface according to the invention is made of metal or of carbon in any of its conductive forms. In a first embodiment, the electrically conductive surface is made of carbon in any of its conductive forms such as graphite, pastes or graphite-based inks, carbon fibers or nanotubes, graphene and reduced graphene oxide, carbon black, glassy carbon, doped diamond e.g. Boron-Doped Diamond (BDD), products pyrolized by polymers, including photoresist. In a second and preferred embodiment, the electrically conductive surface is made of metal. The metal according to the invention can be selected from gold, platinum, titanium, silver, copper, aluminum, zinc, nickel, brass, bronze, calcium, beryllium, rhodium, magnesium, molybdenum, iridium, tungsten, cobalt, cadmium, ruthenium, lithium, iron, palladium, tin, selenium, tantalum, niobium, steel, chromium, lead, vanadium, uranium, zirconium, mercury, derivatives and mixtures thereof.

The metal according to the invention may be resistant to an oxidation potential equal to about 1 V vs Ag/AgCl, or mixtures of said metals. The metal according to the invention can also be selected from the metals stable upon anodic polarization, e.g. 0.8 V vs Ag/AgCl/KCl sat (i.e. an AgCl coated Ag wire immersed in a saturated solution of KCl). The metal according to the invention can also be a noble metal, i.e. a metal resistant to corrosion and oxidation in moist air. In a preferred embodiment, the metal according to the invention may be selected from ruthenium (Ru), rhodium (Rh), palladium (Pd), silver (Ag), osmium (Os), iridium (Ir), platinum (Pt), gold (Au), mercury (Hg), rhenium (Re), copper (Cu), titanium (Ti), niobium (Nb), and tantalum (Ta), derivatives and mixtures thereof. In a most preferred embodiment, the metal according to the invention may be selected from ruthenium (Ru), rhodium (Rh), palladium (Pd), silver (Ag), osmium (Os), iridium (Ir), platinum (Pt), and gold (Au), derivatives and mixtures thereof. Said metal mixtures according to the invention can be homogeneous (e.g., alloys) or derived from the assembly of structures or layers of different metals, or on nanometric scale also (e.g., nanoparticles). In a most preferred embodiment, the electrically conductive surface according to the invention is made of gold.

The electrically conductive surface according to the invention has a certain shape, size and thickness.

In a preferred embodiment, the electrically conductive surface according to the invention has a size between about 1 $nm^2$ and about 10 $cm^2$, preferably between about 1 $\mu m^2$ and about 1 $cm^2$, more preferably between about 10 $\mu m^2$ and about 100 $mm^2$, even more preferably between about 0.1 $mm^2$ and 10 $mm^2$. In a most preferred embodiment, the size of the MIP layer according to the invention is of about 0.80 $mm^2$.

The electrically conductive surface according to the invention can be of any shape. Preferably, it has a rectangular, square or circular shape, preferably a circular shape.

The thickness of the electrically conductive surface according to the invention has a thickness between about 1 nm and about 1 cm, preferably between about 10 nm and about 100 $\mu m$, more preferably between about 10 nm and about 10 $\mu m$, even more preferably between about 100 nm and about 1 $\mu m$.

The MIP layer according to the invention is at least partially coating the electrically conductive surface. Preferably, the MIP layer coats the entire electrically conductive surface, i.e. about 100% of the electrically conductive surface. Alternatively, the MIP layer coats at least 10%, 20%, 30%, 40%, 50%, 60%, 70%, 80%, 90%, 95%, or 99% of the electrically conductive surface, preferably at least 99%. Alternatively, the MIP layer coats no more than 10%, 20%, 30%, 40%, 50%, 60%, 70%, 80%, 90%, 95%, or 99% of the electrically conductive surface.

When using the MIP layer coated electrically conductive surface for the detection of NF molecules in a liquid medium, it is advantageous that the MIP layer entirely covers the electrically conductive surface, or at least the part of the electrically conductive surface used for the detection of NF molecules.

When some parts of the electrically conductive surface are not coated by the MIP layer, the non-coated parts are preferably coated by blocking agents. As used herein, the term "blocking agent" refers to any agent able to prevent the non-specific adhesion of molecules, in particular NF molecules, to the electrically conductive surface. The blocking agent according to the invention can be selected from, for example, BSA, HSA, casein, derivatives and combinations thereof.

In a third aspect, the invention still relates to a Neurotrophic Factor electrode (NF electrode), said electrode comprising a MIP layer coated electrically conductive surface, the MIP layer comprising a m-phenylenediamine (m-PD) polymer and Neurotrophic Factor (NF) imprints.

The NF, the MIP layer and the m-PD are as described in the first aspect described above. The electrically conductive surface and the MIP layer coated electrically conductive surface are as described in the second aspect described above.

As used herein, the term "electrode" refers to an electrical conductor that can be used to make contact with an electrolyte. Therefore, the electrode according to the invention comprises an electrically conductive surface. The electrically conductive surface of the electrode can be made of metal or of carbon in any of his conductive forms, said metal and carbon being as described in the above-mentioned second aspect of the invention. Preferably, the electrically conductive surface is made of gold.

The electrode according to the invention may further comprise a supporting material. Alternatively, the electrode according to the invention do not comprise a supporting material and may comprise of an electrically conductive surface.

The supporting material according to the invention is preferably an electrical insulator. According to the invention, the terms "dielectric", "dielectric material", "electrical insulator" or "insulator" are equivalent and refer to a material whose internal electric charges do not flow freely.

When the electrode comprises a supporting material, the electrically conductive surface is at least partially coating the surface of the supporting material. For example, the electrically conductive surface may coat at least 10%, 20%, 30%, 40%, 50%, 60%, 70%, 80%, 90%, 95%, or 99% of the supporting material, preferably at least 99%. Alternatively, the electrically conductive surface may coat no more than 10%, 20%, 30%, 40%, 50%, 60%, 70%, 80%, 90%, 95%, or 99% of the supporting material. In a particular embodiment, the electrically conductive surface coats the entire supporting material, i.e. about 100% of the supporting material.

The supporting material is preferably an electrical insulator. The electrical insulator according to the invention may be selected from ceramics, glass, plastics, mica, metal oxides, paper, Teflon, rubber-like polymers, polymer composite materials, derivatives and mixtures thereof. Polymer composite material may comprise a central rod made of fiber-reinforced plastic and an outer weathershed made of silicone rubber or ethylene propylene diene monomer rubber (EPDM). Preferably, the electrical insulator is a ceramic. For example, a ceramic can be made from clay, quartz, alumina or feldspar. Preferably, the ceramic according to the invention is selected from alumina ceramics, sapphire ceramics, aluminum nitride ceramics, silicon nitride ceramics, cordierite ceramics, mullite ceramics, steatite ceramics, forsterite ceramics, Yttria ceramics, zirconia ceramics, silicon carbide ceramics, cermet ceramics, variants and mixtures thereof. More preferably, the supporting material according to the invention is an alumina ceramic.

In a preferred embodiment, the NF electrode according to the invention comprises an alumina ceramic supporting material coated with gold.

In another preferred embodiment, the NF electrode according to the invention is a working electrode. As used herein, the term "working electrode" refers to the electrode of a NF sensor, preferably a NF electrochemical sensor, on which the detection of NF molecules is occurring. The NF sensor and NF electrochemical sensor are as described in the fourth aspect of the invention below. In a most preferred embodiment, the NF electrode according to the invention is a working electrode comprising an alumina ceramic supporting material coated with gold.

In a fourth aspect, the invention further relates to a Neurotrophic Factor sensor (NF sensor) comprising at least one MIP layer, and/or at least one MIP layer coated electrically conductive surface, and/or at least one NF electrode. Preferably, the invention concerns a NF sensor comprising one MIP layer, and/or one MIP layer coated electrically conductive surface, and/or one NF electrode. Alternatively, the invention may concern a NF sensor comprising several MIP layers, and/or several MIP layer coated electrically conductive surfaces, and/or several NF electrodes.

The NF sensor can thus comprise at least one MIP layer, preferably one MIP layer. Alternatively, the NF sensor may comprise several MIP layers, preferably 2, 3, 4, 5, 6, 7, 8, 9, or 10 MIP layers.

The NF sensor can also comprise at least one MIP layer coated electrically conductive surface, preferably one MIP layer coated electrically conductive surface. Alternatively, the NF sensor may comprise several MIP layer coated electrically conductive surfaces, preferably 2, 3, 4, 5, 6, 7, 8, 9, or 10 MIP layer coated electrically conductive surfaces.

The NF sensor can still comprise at least one NF electrode, preferably one NF electrode. Alternatively, the NF sensor may comprise several NF electrodes, preferably 2, 3, 4, 5, 6, 7, 8, 9, or 10 NF electrodes.

The Neurotrophic Factor, the MIP layer and the m-PD are as described in the first aspect of the invention above mentioned. The electrically conductive surface and the MIP layer coated electrically conductive surface are as described in the second aspect of the invention above mentioned. The NF electrode is as described in the third aspect of the invention above mentioned.

As used herein, the terms "Neurotrophic factor sensor", "NF sensor", "Neurotrophic Factor detector" and "NF detector" are equivalent and refer to a device that detects the liaison of NF molecules to its MIP layer and responds with a transmitted signal.

Preferably, the NF sensor according to the invention is an electrochemical sensor. As used herein, the term "electrochemical sensor" refers to a device that give information about the concentration of a NF in a liquid medium in real time by coupling a NF selective layer, i.e. a MIP layer imprinted with a NF, to an electrochemical transducer. In this way, the chemical energy of the selective interaction between the NF molecules and the sensor is transduced into an analytically useful signal. The liquid medium is as described in the thirtieth aspect of the invention below.

The NF electrochemical sensor according to the invention may be selected from potentiometric electrochemical sensors in which the electrical magnitude used for transduction of the NF detection is a change of potential, conductometric electrochemical sensors in which the electrical magnitude used for transduction of the NF detection is a change of conductance, impedimetric electrochemical sensors in which the electrical magnitude used for transduction of the NF detection is a change of impedance, voltammetric electrochemical sensors in which the electrical magnitude used for transduction of the NF detection is a change of current for an electrochemical reaction with the applied voltage, or amperometric electrochemical sensors in which the electrical magnitude used for transduction of the NF detection is a change of current for an electrochemical reaction with time at a fixed applied potential.

In a preferred embodiment, the NF electrochemical sensor according to the invention is an amperometric electrochemical sensor. Different amperometric methods may be used to make electrochemical measurements such as normal pulse voltammetry, cyclic voltammetry or differential pulse voltammetry. In a most preferred embodiment, differential pulse voltammetry is used for determining a response from NF amperometric electrochemical sensor. As used herein, the terms "differential pulse voltammetry", "DPV", "differential pulse polarography" and "DPP" are equivalent and refer to a voltammetry method used to make electrochemical measurements and a derivative of linear sweep voltammetry or staircase voltammetry, with a series of regular voltage pulses superimposed on the potential linear sweep or stairsteps. The current is measured immediately before each potential change, and the current difference is plotted as a function of potential. By sampling the current just before the potential is changed, the effect of the charging current can be decreased.

The NF sensor according to the invention, preferably a NF electrochemical sensor, more preferably an amperometric electrochemical sensor, even more preferably a differential pulse voltammetry electrochemical sensor, may comprise at least one electrically conductive surface, preferably at least two electrically conductive surfaces, more preferably at least three electrically conductive surfaces. Alternatively, the NF sensor according to the invention, preferably a NF electrochemical sensor, more preferably an amperometric electrochemical sensor, even more preferably a differential pulse voltammetry electrochemical sensor, may comprise between 1 and 10 electrically conductive surfaces, preferably between 1 and 5 electrically conductive surfaces, even more preferably between 2 and 4 electrically conductive surfaces. For example, the NF sensor according to the invention, preferably a NF electrochemical sensor, more preferably an amperometric electrochemical sensor, even more preferably a differential pulse voltammetry electrochemical sensor, may comprise 1, 2, 3, 4 electrically conductive surfaces. In a most preferred embodiment, the NF sensor according to the invention, preferably a NF electrochemical sensor, more preferably an amperometric electrochemical sensor, even more preferably a differential pulse voltammetry electrochemical sensor, comprises three electrically conductive surfaces. The electrically conductive surfaces are as described in the second aspect of the invention above mentioned.

In a preferred embodiment, the MIP layer according to the invention coats at least one electrically conductive surface of the NF sensor according to the invention, preferably a NF electrochemical sensor, more preferably an amperometric electrochemical sensor, even more preferably a differential pulse voltammetry electrochemical sensor. In a particular embodiment, the MIP layer according to the invention coats several electrically conductive surfaces, preferably between 2 and 10 electrically conductive surfaces, more preferably between 2 and 5 electrically conductive surfaces, even more preferably 2, 3 or 4 electrically conductive surfaces of the NF sensor according to the invention, preferably a NF electrochemical sensor, more preferably an amperometric electrochemical sensor, even more preferably a differential pulse voltammetry electrochemical sensor. It is understood that the number of electrically conductive surfaces of the sensor coated by a MIP layer according to the invention cannot be greater than the total number of electrically conducting surfaces of said sensor. In a preferred embodiment, the MIP layer according to the invention coats one electrically conductive surface of the NF sensor according to the invention, preferably a NF electrochemical sensor, more preferably an amperometric electrochemical sensor, even more preferably a differential pulse voltammetry electrochemical sensor. In an even more preferred embodiment, the NF sensor according to the invention, preferably a NF electrochemical sensor, more preferably an amperometric electrochemical sensor, even more preferably a differential pulse voltammetry electrochemical sensor has three electrically conductive surfaces and one is coated by a MIP layer according to the invention. Preferably, the electrically conductive surface coated by the MIP layer is made of gold.

When the NF sensor according to the invention, preferably a NF electrochemical sensor, more preferably an amperometric electrochemical sensor, even more preferably a differential pulse voltammetry electrochemical sensor, presents several electrically conductive surfaces coated by a MIP layer, the MIP layers can be imprinted by the same neurotrophic factor or by different neurotrophic factors.

Alternatively, the NF sensor according to the invention, preferably a NF electrochemical sensor, more preferably an amperometric electrochemical sensor, even more preferably a differential pulse voltammetry electrochemical sensor, may comprise at least one electrode, preferably at least two electrodes, more preferably at least three electrodes. Alternatively, the NF sensor according to the invention, preferably a NF electrochemical sensor, more preferably an amperometric electrochemical sensor, even more preferably a differential pulse voltammetry electrochemical sensor, may comprise between 1 and 10 electrodes, preferably between 1 and 5 electrodes, even more preferably between 2 and 4 electrodes. For example, the NF sensor according to the invention, preferably a NF electrochemical sensor, more preferably an amperometric electrochemical sensor, even more preferably a differential pulse voltammetry electrochemical sensor, may comprise 1, 2, 3, or 4 electrodes. In a most preferred embodiment, the NF sensor according to the invention, preferably a NF electrochemical sensor, more preferably an amperometric electrochemical sensor, even more preferably a differential pulse voltammetry electrochemical sensor, comprises three electrodes. The electrodes are as described in the third aspect of the invention above mentioned.

Preferably, at least one of the electrodes, at least two of the electrodes, at least three of the electrodes of the NF sensor according to the invention, preferably a NF electrochemical sensor, more preferably an amperometric electrochemical sensor, even more preferably a differential pulse voltammetry electrochemical sensor is a NF electrode, preferably a NF working electrode. The NF electrodes and NF working electrodes are as described in the third aspect of the invention above mentioned. In a particular embodiment, several of the electrodes of the NF sensor according to the invention, preferably a NF electrochemical sensor, more preferably an amperometric electrochemical sensor, even more preferably a differential pulse voltammetry electrochemical sensor are NF electrodes, preferably NF working electrodes, preferably between 2 and 10 of the electrodes are NF electrodes, preferably NF working electrodes, more preferably between 2 and 5 of the electrodes are NF electrodes, preferably NF working electrodes, even more preferably 2, 3 or 4 of the electrodes are NF electrodes, preferably NF working electrodes. It is understood that the number of NF electrodes according to the invention cannot be greater than the total number of electrodes of said sensor. In a preferred embodiment, one of the electrodes of the NF sensor according to the invention, preferably a NF electrochemical sensor, more preferably an amperometric electrochemical sensor, even more preferably a differential pulse voltammetry electrochemical sensor is a NF electrode, preferably a NF working electrode. In an even more preferred embodiment, the NF sensor according to the invention, preferably a NF electrochemical sensor, more preferably an amperometric electrochemical sensor, even more preferably a differential pulse voltammetry electrochemical sensor comprises three electrodes and one of them is a NF electrode, preferably a NF working electrode, even more preferably a NF working electrode made of alumina ceramic and gold coated.

When the NF sensor according to the invention, preferably a NF electrochemical sensor, more preferably an amperometric electrochemical sensor, even more preferably a differential pulse voltammetry electrochemical sensor, present several NF electrodes, preferably NF working electrodes, the MIP layers of the different electrodes, preferably NF working electrodes, can be imprinted by the same NF or by different NFs.

In the NF sensor according to the invention, preferably a NF electrochemical sensor, more preferably an amperometric electrochemical sensor, even more preferably a differential pulse voltammetry electrochemical sensor, the at least one NF electrode, preferably the NF electrode, more preferably the NF working electrode, can be connected, or is connectable, to an electrically conductive wire, e.g. a copper wire, in turn connected, or connectable, to a suitable current detector composed for example by a potentiostat integrated with a function generator and suitable systems of sampling of the intensity of current/electric charge and of data acquisition/processing. To such end, any potentiostat system of prototype or commercial type, suitable for the control voltage bias between electrodes of an electrochemical cells, can be employed. As used herein, the term "electrochemical cell" refers to a device capable of either generating electrical energy from chemical reactions or using electrical energy to cause chemical reactions. Such electrodes include, without limitation, a working electrode, preferably a NF working electrode, a counter electrode, for example made of alumina ceramic coated with gold or of an inert conductor such as Platinum or Carbone, and a reference electrode, for example a silver chloride electrode such as Ag/AgCl/KClsat—a silver wire coated with a layer of solid silver chloride, immersed in the saturated potassium chloride, or a pseudo reference electrode, for example an Ag/AgCl— a silver wire coated with a layer of solid silver chloride. As used herein, the term "reference electrode" refers to an electrode which has a stable and well-known electrode potential. As used herein, the terms "counter electrode" and "auxiliary electrode" are equivalent and refer to an electrode used in a three electrodes electrochemical cell for voltammetric analysis or other reactions in which an electric current is expected to flow. By means of the auxiliary electrode, a requested voltage is applied to the working electrode.

This configuration allows the potential of the working electrode to be measured against a known reference electrode without compromising the stability of that reference electrode by passing current over it.

In a preferred embodiment, the NF sensor according to the invention, preferably a NF electrochemical sensor, more preferably an amperometric electrochemical sensor, even more preferably a differential pulse voltammetry electrochemical sensor, comprise a NF electrode, preferably a NF working electrode, a reference electrode and a counter electrode, the NF working electrode being preferably an electrode made of alumina ceramic and gold coated.

In a most preferred embodiment, when the NF sensor comprises more than 3 electrodes, it comprises one counter electrode, one reference electrode and several working electrodes, preferably NF working electrodes.

Optionally, the NF sensor according to the invention, preferably a NF electrochemical sensor, more preferably an amperometric electrochemical sensor, even more preferably a differential pulse voltammetry electrochemical sensor, comprise an electrically conductive surface coated by a Non-molecularly Imprinted Polymer (NIP) layer or a NIP electrode. The NIP electrode of the NF sensor according to the invention, preferably a NF electrochemical sensor, more preferably an amperometric electrochemical sensor, even more preferably a differential pulse voltammetry electrochemical sensor, may be a NIP counter electrode, a NIP reference electrode or a supplementary NIP working electrode.

As used herein, the term "Non-molecularly Imprinted Polymer layer" or "NIP layer" refers to a layer of polymer produced exactly in the same conditions as the MIP layer but in the absence of the neurotrophic factor or in the presence of the neurotrophic factor but without removing the neurotrophic factor from the polymer at the end of the polymerization process. A NIP layer will have, for example, the same thickness and polymer composition as the corresponding MIP layer. As used herein, the term NIP electrode refers to an electrode which conductive surface is at least in part coated by a NIP layer, preferably the all conductive surface of the electrode is coated by a NIP layer.

The NF electrochemical sensor according to the invention, more preferably an amperometric electrochemical sensor, even more preferably a differential pulse voltammetry electrochemical sensor, may be an electrochemical sensor of the classical type with a cell in which the different electrodes are separated and singularly insertable/replaceable, the cell containing the electrolytic solution. Preferably, the NF electrochemical sensor, more preferably an amperometric electrochemical sensor, even more preferably a differential pulse voltammetry electrochemical sensor, is of an integrated and miniaturized form, preferably on chip on which the electrodes are imprinted by serigraphic processes, i.e. screen-printed electrodes, and/or by deposition/sputtering/etching of conductors and insulators, and/or by photolithography followed by pyrolysis, i.e. pyrolyzed photoresist carbon electrodes, and the like.

In a most preferred embodiment, the NF electrochemical sensor according to the invention, more preferably an amperometric electrochemical sensor, even more preferably a differential pulse voltammetry electrochemical sensor, is a Screen Printed Electrochemical sensor (SPE sensor).

As used herein, the term "Screen Printed Electrochemical Sensor", "SPE" and "Screen Printed Electrode" are equivalent and refer to a chemically inert substrate on which three electrodes, including a working electrode, a reference electrode and a counter electrode, are printed through screen printing methodology. The working electrode is the principal electrode on which electrochemical reactions are performed, while the reference electrode and counter electrode are used to complete the electronic circuit. The chemical event on the screen printed electrode, i.e. interaction of NF molecules with the imprints of the MIP layer, is converted into a detectable signal with the integration of a transducer element, i.e. the electrochemical transduction. The fabrication of an electrochemical screen printed sensor usually involves three steps: fabrication of the screen printed electrode itself, surface design of the screen printed electrode and subsequently utilization for a sensing application.

The inks used in screen printed electrode fabrication comprises particles, polymeric binder and other additives for improved dispersion, printing and adhesion process. The exact ink formulation and composition are patented by the respective companies and may not be disclosed to the users. The variation in the ink composition such as types, size or loading of particles strongly influence the electron transfer process and change the overall performance of the designed screen printed sensor. The invention can be implemented by any type of SPE. Preferred SPE according to the invention are SPE produced by BVT Technologies.

The SPE according to the invention can be selected from preanodized screen printed carbon electrodes and metal oxide based screen printed electrodes. Preferably, the SPE according to the invention is a gold coated screen printed electrode.

In a most preferred embodiment, the NF sensor according to the invention is a NF SPE, said SPE being made of a non-conductive substrate, preferably alumina ceramic, the working electrode of said SPE having a gold electrically conductive surface coated by a MIP layer imprinted by a NF. The non-conductive substrate is as described in the third aspect of the invention above mentioned. Preferably, the counter electrode is also a gold coated electrode. Preferably, the reference electrode is a silver electrode coated with silver chloride. Preferably, the SPE is connected to a potentiostat (reader), which measures currents appearing between the NF working electrode and the counter electrode, or potentials between the NF working electrode and the reference electrode. In a particular embodiment, the reference electrode or the counter electrode of the NF SPE, preferably the reference electrode of the NF SPE is coated by a NIP.

The NF sensor according to the invention may be very sensitive and specific of the NF or the combination of NF, preferably BDNF, used to imprint the MIP layer. The NF sensor according to the invention may have a limit of detection (LOD) inferior to about 10 ng/ml, preferably to about 1 ng/ml, more preferably to about 0.1 ng/ml, even more preferably to about 0.05 ng/ml. In a most preferred embodiment, the NF sensor according to the invention has a LOD of about 0.04 ng/ml.

As used herein the terms "Limit of Detection", "LOD", "detection limit", "lower limit of detection" are equivalent and refer to the lowest quantity of a substance that can be distinguished from the absence of that substance (i.e. a blank value) with a stated confidence level (generally of 99%). The detection limit can be estimated from the mean of the blank, the standard deviation of the blank and some confidence factor. Another consideration that affects the detection limit is the accuracy of the model used to predict concentration from the raw analytical signal. The LOD can also be calculated according to the following formula: LOD=3*S/b, where S is standard deviation of the regression residuals and b is the slope of the regression line.

The NF sensor according to the invention may have a limit of quantitation (LOQ) lower than about 100 ng/ml, preferably to about 10 ng/ml, more preferably to about 1 ng/ml, even more preferably to about 0.5 ng/ml, still more preferably to about 0.2 ng/ml. In a most preferred embodiment, the NF sensor according to the invention has a LOQ of about 0.12 ng/ml.

As used herein, the term "Limit of Quantitation" or "LOQ" may refers to the limit at which the difference between two distinct concentrations can be reasonably discerned. Preferably, the term "Limit of Quantitation" or "LOQ" refers to the lowest analyte concentration that can be quantitatively detected with a stated accuracy and precision. The LOQ can be calculated according to the following formula: LOQ=10*S/b, where S is the standard deviation of the regression residuals and b is the slope of the regression line.

The NF sensor according to the invention may also be very selective, i.e. it rebinds selectively the target NF, preferably BDNF, with respects to interfering molecules with slightly different size and pI (Isoelectric point). The interfering molecules for the NF, preferably BDNF, can be for example the Cerebral Dopamine Neurotrophic Factor (CDNF), Mesencephalic Astrocyte-Derived Neurotrophic Factor (MANF) and mouse recombinant mCD48 antigen.

The NF sensor according to the invention may have a selectivity at least 1.5 time higher, preferably 2 times higher, for the target NF, preferably BDNF, than to any interfering molecule. In a particular embodiment, the selectivity of the NF sensor for the target NF, preferably BDNF, is 3 times higher, 5 times higher, 10 times higher, than to any interfering molecule.

In a fifth aspect, the invention relates to a method for preparing a MIP layer coated electrically conductive surface, wherein the MIP layer comprises a m-PD polymer and NF imprints, and wherein the method comprises the following steps:

1) formation of a cleavable linking layer on the electrically conductive surface;
2) immobilization of the NF molecules on the cleavable linking layer;
3) polymerization of m-PD on the NF-immobilized electrically conductive surface thereby forming a polymeric layer coating said electrically conductive surface with entrapped NF; and
4) cleavage of the cleavable linking layer thereby removing the NF molecules from the polymeric layer and forming the MIP layer.

In a sixth aspect, the invention relates to a method for preparing a NF electrode, wherein the method comprises the following steps:

1) formation of a cleavable linking layer on the electrically conductive surface of the electrode;
2) immobilization of the NF molecules on the cleavable linking layer;
3) polymerization of m-PD on the NF-immobilized electrically conductive surface of the electrode thereby forming a polymeric layer coating the NF electrode; and
4) cleavage of the cleavable linking layer thereby removing the NF molecules from the polymeric layer and forming the MIP layer.

In a seven aspect, the invention further relates to a method for preparing a NF Sensor, wherein the method comprises the following steps:

1) formation of a cleavable linking layer on an electrically conductive surface of the sensor, preferably on an electrode of the sensor, more preferably on a working electrode of the sensor;
2) immobilization of the NF molecules on the cleavable linking layer;
3) polymerization of m-PD on the NF-immobilized electrically conductive surface of the sensor, preferably on an electrode of the sensor, more preferably on a working electrode of the sensor, thereby forming a polymeric layer coating with entrapped NF on an electrically conductive surface of the sensor, preferably an electrode of the sensor, more preferably a working electrode of the sensor; and
4) cleavage of the cleavable linking layer thereby removing the NF molecules from the polymeric layer and forming the MIP layer.

In an eighth aspect, the invention further relates to a method for preparing a NF SPE, wherein the method comprises the following steps:

1) formation of a cleavable linking layer on an electrically conductive surface of the SPE, preferably on an electrode of the SPE, more preferably on the working electrode of the SPE;
2) immobilization of the NF molecules on the cleavable linking layer;
3) polymerization of m-PD on the NF-immobilized electrically conductive surface of the SPE, preferably on an electrode of the SPE, more preferably on the working electrode of the SPE thereby forming a polymeric layer with entrapped NF coating an electrically conductive surface of the SPE, preferably an electrode of the SPE, more preferably the working electrode of the SPE; and
4) cleavage of the cleavable linking layer thereby removing the NF molecules from the polymeric layer and forming the MIP layer.

The Neurotrophic Factor, the MIP layer and the m-PD are as described in the first aspect above mentioned. The electrically conductive surface and the MIP layer coated electrically conductive surface are as described in the second aspect above mentioned. The electrode, the working electrode and the NF electrode are as described in the third aspect above mentioned. The NF sensor, the SPE and the NF SPE are as described in the fourth aspect above mentioned.

In the first step of the method for preparing a MIP layer coated electrically conductive surface, method for preparing a NF electrode, method for preparing a NF Sensor, or method for preparing a NF SPE, a cleavable linking layer is respectively formed on the electrically conductive surface, on the electrically conductive surface of the electrode, on an electrically conductive surface of the sensor, or on an electrically conductive surface of the SPE.

As used herein, the term "linking layer" refers to any molecule or group of molecules deposited on the electrically conductive surface and able to covalently link the NF molecules to the electrically conductive surface. The nature of the linking layer allows charge transfer between the electrically conductive surface and the polymerization solution and does not impair the quality of the MIP layer or its adhesion to the electrically conductive surface.

The linking layer can be constituted of only one type of linking molecules, the layer of this linking molecule being formed on the electrically conductive surface at step one of the above mentioned methods. The linking layer can also be constituted of several types of linking molecules, i.e. a multilayer of different linking molecules is formed on the electrically conductive surface at step one of the above mentioned method. For example, 2, 3, 4, or 5 linking molecules are constituting the linking layer. In a preferred embodiment, the linking layer is constituted by 1 or 2 types of linking molecules. In a most preferred embodiment, the linking layer is formed by two types of linking molecules, a layer of the first linking molecule is first covalently linked to the electrically conductive surface and a second layer of the second linking molecule is then covalently linked to the first layer of linking molecules.

The linking layer according to the invention is cleavable. The linking layer can be cleaved by cleaving the bond(s) between a linking molecule and the electrically conductive surface, and/or by cleaving the bond(s) between a linking molecule and the NF molecules, and/or by cleaving at least one bond between two linking molecules when the linking layer comprises at least two linking molecules, and/or by cleaving at least one internal bond of a linking molecule.

In a preferred embodiment, at least one of the linking molecules, preferably one of the linking molecules, is cleavable, i.e. present at least one internal cleavable bond, preferably present one internal cleavable bond, and the linking layer is cleaved by cleaving the at least one internal bond, preferably the internal bond, of at least one cleavable linking molecule, preferably of the cleavable linking molecule.

The cleavable linking molecule according to the invention may be a chemically cleavable molecule or an enzymatic cleavable molecule, preferably a chemically cleavable molecule. When using a cleaving agent, it is essential to ensure that respective cleavage agents will not affect the polymer and the SPEs. From that respect, enzymatic cleavable agents (i.e. enzymes) may be particularly problematic for protein removal due to the following reasons: (i) since an enzymatic protein is a macromolecule, its access to the linking molecule cleavage site after polymerization can be sterically hindered; (ii) the enzymatic cleavage may decompose the target protein as well, leaving behind small fragments of the protein than can be difficult to remove from the polymer matrix; (iii) it is also possible that the enzymatic protein itself may be difficult to remove from the polymer and can subsequently disturb the rebinding process. Therefore, the chemically cleavable molecules are preferred. Preferably, the chemically cleavable molecule is selected from nucleophile/base sensitive linkers such as halogens nucleophiles, oxygen nucleophiles, thiols nucleophiles and nitrogen nucleophiles that are cleavable by nucleophilic/basic reagents, reduction sensitive linkers such as linkers having a disulfide bridge or azo compounds that are cleavable by reducing agents, photocleavable linkers such as ortho-nitrobenzyl derivatives or phenacyl ester derivatives that are cleavable by photo-irradiation, acid cleavable linkers, azide cleavable linkers, metal assisted cleavable linkers, and oxidation sensitive linkers. More preferably, the cleavable linking molecule according to the invention is a reduction sensitive linker, preferably a linker having a disulfide bridge. The cleavable linking molecule can be as described in Leriche G et al. (Bioorganic & Medicinal Chemistry, 2012, 20, pp. 571-582) herein incorporated by reference.

The cleavable bond of the cleavable linking molecule can be any kind of cleavable bond well known from the man skilled in the art. Preferably, the cleavable bond of the cleavable linking molecule is a disulfide bond.

When the linking layer is constituted by 2 types of linking molecules, the cleavable linking molecule can be the one directly bound to the electrically conductive surface or the one directly linked to the NF molecules, preferably, the cleavable linking molecule is the one directly linked to the NF molecules.

In a preferred embodiment, the cleavable linking layer is constituted of 2 types of linking molecules, the one directly linked to the NF being a cleavable linking molecule, said cleavable linking molecule having a cleavable disulfide bond.

In a most preferred embodiment, the electrically conductive surface is made of gold and the formation of a cleavable linking layer on the gold surface according to step 1 comprises the following steps:

1) formation of an amino-functionalized monolayer, preferably a 4-aminothiophenol (4-ATP) monolayer, on the gold surface; and 2) formation of a 3,3'-dithiobis(sulfosuccinimidyl propionate) (DTSSP) monolayer by covalently linking DTSSP molecules to the amino-functionalized monolayer, preferably a 4-ATP monolayer, DTSSP having a cleavable disulfide bond, thereby obtaining a cleavable linking layer on the gold surface. In this cleavable linking layer, the amino-functionalized monolayer, preferably 4-ATP molecules bind to the gold surface through Au—S covalent bonds and DTSSP molecules bind to the amino-functionalized monolayer, preferably 4-ATP, through amide bonds. The amide bond is formed between the amino group of 4-ATP and the sulfo-NHS ester group of DTSSP.

The formation of a 4-ATP monolayer on the gold surface can be obtained by immersing the gold surface in an ethanolic solution, preferably at a concentration of at least 95%, comprising between about 0.01 M and about 1 M of 4-ATP, preferably about 0.1 M of 4-ATP, for between about 10 minutes and about 5 hours, preferably for about 1 hour.

The formation of the DTSSP monolayer on the 4-ATP monolayer can be obtained by immersion of 4-ATP modified gold surface in a Phosphate Buffered Saline (PBS) solution at a concentration of between about 0.001 M and about 0.1 M, preferably 0.01 M, having a pH between about 7 and about 7.8, preferably of about 7.4, and between about 5 mM and about 30 mM, preferably about 10 mM of DTSSP for between about 10 min and about 1 hour, preferably about 30 minutes.

In the second step of the method for preparing a MIP layer coated electrically conductive surface, method for preparing a NF electrode, method for preparing a NF Sensor, or method for preparing a NF SPE, NF molecules are immobilized on the linking layer, preferably by formation of bonds between the most superficial linking molecules and the NF molecules. Preferably, at least a part of these bonds are covalent bonds. The most superficial linking molecules is the layer of linking molecules that is the most distant from the electrically conductive surface.

The covalent bonds between the NF molecules and the most superficial linking molecules can be any type of covalent bond according to the nature of the NF molecules and linking molecules involved. Preferably, the bond between the NF molecules and the most superficial linking molecules are amide bonds.

In a preferred embodiment, the most superficial linking molecules are DTSSP molecules and, amide bonds are formed predominantly through lysine residues of the NF, preferably BDNF.

The immobilization of NF on the cleavable linking layer can be obtained by immersion of the electrically conductive surface, preferably a gold surface, having a cleavable linking layer, preferably a 4-ATP/DTSSP cleavable linking layer, in a PBS solution at a concentration between about 0.001 M and about 0.1 M, preferably about 0.01 M, having a pH between about 7 and about 7.8, preferably of about 7.4, and comprising between about 10 µg/ml and about 50 µg/ml, preferably 25 µg/ml of NF, preferably BDNF, for between about 10 min and about 1 h, preferably about 30 minutes, preferably at room temperature. Preferably, the solution of NF has such a concentration than only between about 1 and about 5 µl, preferably about 2 µl of said concentrated solution must be added to the PBS solution to reach the proper final concentration of NF.

In the third step of the method for preparing a MIP layer coated electrically conductive surface, method for preparing a NF electrode, method for preparing a NF Sensor, or method for preparing a NF SPE, m-PD is polymerized on the NF-immobilized electrically conductive surface.

m-PD can be polymerized by any method well known from the man skilled in the art. As used herein the term "polymerization" refers to a process of reacting monomer molecules together in a chemical reaction to form polymer chains or three-dimensional networks. Preferably, the polymerization of m-PD is an electropolymerization.

As used herein, the term "electropolymerization" or "electrodeposition" refers to a polymerization method in which a polymer layer with a certain thickness is obtained by controlling the number of cycles or the current that is applied to the electrode. In an electrochemical polymerization, the monomer polymerization is usually activated, i.e. radicals of the monomers are generated by the potential applied to the electrode. The main advantages of the electropolymerization are the formation of a polymer film directly on the electrode surface and the possibility of the polymer thickness to be controlled by adjusting the electrical charge passed through the electrode.

The electropolymerization according to the invention can be selected from potentiostatic, galvanostatic, potential cycling, and potential pulse methods, preferably the electropolymerization is performed under a potentiostatic conditions.

The electropolymerization according to the invention can be performed by cathodic reduction or anodic oxidation, preferably the electropolymerization is an anodic oxidation.

In a preferred embodiment, the electropolymerization is performed in the presence of about 5 mM and about 50 mM of m-PD, preferably about 7 mM and about 25 mM of m-PD, more preferably about 7 mM and about 15 mM of m-PD, even more preferably the electropolymerization is performed in the presence of about 10 mM of m-PD.

In another preferred embodiment, the electropolymerization is performed by an electrochemical workstation (potentiostat) in an electrochemical cell at a constant potential versus a reference electrode. Preferably, the constant potential applied is of a value between about 0.1 and about 0.4 V, preferably between about 0.2 and about 0.3 V, more preferably between about 0.24 V and about 0.28 V, even more preferably the constant potential applied is of about 0.26 V. Preferably, the reference electrode is an Ag/AgCl reference electrode.

In still another preferred embodiment, the electropolymerization is performed until an electric charge of between about 0.5 mC/cm$^2$ and about 5 mC/cm$^2$, preferably between about 1 mC/cm$^2$ and about 3 mC/cm$^2$, more preferably between about 1.5 mC/cm$^2$ and about 2.5 mC/cm$^2$, even more preferably until an electric charge of about 2 mC/cm$^2$ has been passed through the NF-immobilized electrically conductive surface, preferably the BDNF-immobilized gold surface.

The m-PD can be polymerized on the NF-immobilized electrically conductive surface, preferably BDNF-immobilized gold surface, by immersing the NF-immobilized electrically conductive surface, preferably BDNF-immobilized gold surface, in a PBS solution at a concentration between about 0.001 M and about 0.1 M, preferably about 0.01 M, having a pH between about 7 and about 7.8, preferably of about 7.4, and comprising between about 7 mM and about 15 mM of m-PD, preferably about 10 mM of m-PD, by an electrochemical workstation in an electrochemical cell at a constant potential between about 0.2 V and about 0.3 V, preferably of about 0.26 V, versus a reference electrode, preferably an Ag/AgCl reference electrode, until an electric charge of between about 1 mC/cm$^2$ and about 3 mC/cm$^2$, preferably about 2 mC/cm$^2$, has been passed through the NF-immobilized electrically conductive surface, preferably the BDNF-immobilized gold surface.

In the fourth step of the method for preparing a MIP layer coated electrically conductive surface, method for preparing a NF electrode, method for preparing a NF Sensor, or method for preparing a NF SPE, the linking layer is cleaved thereby removing the NF molecules from the polymeric layer and obtaining a NF imprinted MIP layer.

The cleavage of the linking layer can be obtained by immersion of the polymeric layer coated electrically conductive surface in a solution destabilizing the cleavable bond of the cleavable linking molecule. Preferably, the cleavable bond is a disulfide bond and the cleavage of the linking layer can be obtained by immersion of the polymeric layer coated electrically conductive surface in a solution capable to reduce disulfide bonds.

The solution capable to reduce disulfide bonds according to the invention can be selected from 2-mercaptoethanol or β-mercaptoethanol, dithiothreitol (DTT), tris(2-carboxyethyl)phosphine (TCEP), Tris(3-hydroxypropyl)phosphine (THPP), derivatives or mixtures thereof. Preferably, the solution capable to reduce disulfide bonds according to the invention is 2-mercaptoethanol.

The linking layer, preferably the 4-ATP/DTSSP linking layer, can be cleaved by sequential immersion of the polymeric layer coated electrically conductive surface in an ethanolic solution, preferably at a concentration of at least 95%, comprising between about 0.01 M and about 1 M, preferably between 0.05 and 0.3 M, more preferably between about 0.08 M and 0.2 M of 2-mercaptoethanol, in a most preferred embodiment about 0.1 M of 2-mercaptoethanol for between about 5 hours and about 20 hours, preferably for about 7 hours and about 15 hours, even more preferably for about 10 hours followed by an acetic acid aqueous solution concentrated at between about 2% and about 20%, preferably between 5% and 15%, even more preferably concentrated at about 10% for between about 10 min and about 1 hour, preferably for about 30 minutes.

After cleavage of the linking layer, the part of the linking layer that binds to the electrically conductive surface stays in the MIP layer. In particular, with a 4-ATP/DTTSSP linking layer, the molecule that stays in the MIP layer is sulfosuccinimidyl 1-thiopropionate.

The step of cleaving the cleavable linking layer substantially remove the NF molecules, preferably BDNF molecules, from the polymeric layer, thereby forming imprints and obtaining a MIP layer. By substantially removing the NF molecules, it is intended that at least 50%, preferably at least 60%, more preferably at least 70%, still preferably at least 80%, yet preferably at least 90%, even more preferably at least 95% of the NF molecules are removed from the MIP layer. In a particular embodiment, at least 99% of the NF molecules are removed from the MIP layer.

In an additional step, the method for preparing a MIP layer coated electrically conductive surface, method for preparing a NF electrode, method for preparing a NF Sensor, or method for preparing a NF SPE, may comprise prior to the first step of the methods above described, a step of cleaning the electrically conductive surface. Preferably, the electrically conductive surface is electrochemically cleaned. This step insures the electrochemical cleanness and stability of the electrically conductive surface prior to the polymerization. It may also improve the reproducibility of the electropolymerization. To clean the electrically conductive surface, the electrically conductive surface can be immersed in a solution of $H_2SO_4$, preferably at a concentration of between about 0.01 M and about 1 M, preferably about 0.1 M, and the potential is cycled between about 0.005 V and about 2 V, preferably between about 0.1 V and about 1.15 V, versus a reference electrode, preferably an Ag/AgCl reference electrode, at a scan rate of between about 70 and about 130 mV/s, preferably at a scan rate of about 100 mV/s, until the voltammograms are reproducible, i.e. the current peaks are getting to about the same height and position during at least 3 cycles, preferably at least 5 cycles, which indicates that the electrically conductive surface, preferably gold surface, is stable and free of contaminants, and/or for between about 10 cycles and about 20 cycles, preferably for about 15 cycles.

In another additional step, the method for preparing a MIP layer coated electrically conductive surface, method for preparing a NF electrode, method for preparing a NF Sensor, or method for preparing a NF SPE, may comprise after the step of cleaving the linking layer, a step of washing the MIP layer coated electrically conductive surface. Preferably the MIP layer coated electrically conductive surface is washed with water, more preferably with ultrapure water.

The washing step may be obtained by immersing the polymeric layer coated electrically conductive surface in water, preferably ultrapure water, for about 1 min to about 30 min, preferably for about 10 min, under agitation, preferably at a speed comprised between about 300 rpm and about 900 rpm, more preferably at a speed of about 600 rpm. For such an agitation, a vortex can be used, or any other similar device well known from the man skilled in the art.

In yet another additional step, the method for preparing a MIP layer coated electrically conductive surface, method for preparing a NF electrode, method for preparing a NF Sensor, or method for preparing a NF SPE, may further comprise, after the step of washing or directly after the cleavage step, a step of drying the MIP layer coated electrically conductive surface. Preferably, the MIP layer coated electrically conductive surface is dried by a method selected from the group consisting of nitrogen flow or oil free compressed air, preferably by nitrogen flow.

In a ninth aspect, the invention relates a MIP layer coated electrically conductive surface directly obtained by the above described method for preparing a MIP layer coated electrically conductive surface.

In a tenth aspect, the invention also relates to a NF electrode directly obtained by the above described method for preparing a NF electrode.

In an eleventh aspect, the invention further relates to a NF sensor directly obtained by the above described method for preparing a NF sensor.

In a twelfth aspect, the invention still relates to a NF SPE directly obtained by the above described method for preparing a NF SPE.

In a thirteenth aspect, the invention also relates to a method, preferably an in-vitro method, of detection of a NF in a liquid medium or of measuring the concentration of a NF in a liquid medium, the method comprising contacting a NF sensor with said liquid medium. Preferably the NF is BDNF. Preferably, the NF sensor is a NF SPE.

In a preferred embodiment, the invention relates to a method, preferably an in-vitro method, of detection of BDNF or of measuring the concentration of BDNF in a liquid medium, said method comprising contacting a BDNF SPE with said liquid medium.

The NF and the BDNF are as described in the first aspect of the invention above mentioned. The NF sensor is as described in the fourth aspect of the invention above mentioned or in the eleventh aspect of the invention above mentioned. The NF SPE and the BDNF SPE are as described in the fourth aspect of the invention above mentioned or in the twelfth aspect of the invention above mentioned.

The liquid medium according to the invention can be any liquid. Preferably, the liquid medium according to the invention is selected from water sample, a milk sample, a beverage sample, a liquid sample from a patient, and a cell culture medium, preferably the supernatant of a cell culture medium. More preferably, the liquid medium is a sample from a patient.

The patient according to the invention can be any animal. In particular, the patient according to the invention can be a bird, preferably selected from parrot, fowl, poultry such as turkeys, chickens, ducks, geese, guinea fowl. Preferably, the patient according to the invention is a mammal, more preferably selected from cattle, goat, sheep, horse, pig, cat, dog, rabbit, mouse, rat, guinea-pig, zebu, donkey, buffalo, camel, lama yak, alpaca, ferret, reindeer, deer, moose, elephant, squirrel, elk, mink, hamster, chinchilla, bison, gerbil, monkey, primate and human. In a most preferred embodiment, the patient is human.

The human patient according to the invention can be an infant, a child or an adult, preferably an adult of at least 30 years old, more preferably an adult of at least 40 years old, still preferably an adult of at least 50 years old, even more preferably an adult of at least 60 years old. In a particular embodiment, the human patient according to the invention is an adult of at least 55, 60, 65, 70, 75, 80, 85 years old.

The sample from a patient, preferably a human, according to the invention is a body fluid, preferably selected from a blood sample, a plasma sample, a serum sample, a lymph sample, a urine sample, a saliva sample, a cerebrospinal fluid sample and any other brain sample, more preferably a sample selected from a blood sample, a plasma sample, a serum sample, and a cerebrospinal fluid sample, even more preferably the sample from a patient is a serum sample.

In a particular embodiment, the NF sensor, preferably a NF SPE, more preferably a BDNF SPE, can be implanted in a patient, preferably a human. Preferably, the implanted NF sensor can measure the presence or the concentration of a NF in the blood. Such an implanted NF sensor allows a real time measurement of NF concentration in the blood.

The detection and/or measurement of the concentration of NF, preferably BDNF, with a NF sensor, preferably a NF SPE, more preferably a BDNF SPE, in a liquid media, preferably a sample from a patient, preferably a human patient, more preferably a serum sample from a human patient, comprises a pre-measurement phase and a measurement phase.

The premeasurement phase includes the initial sensor reading or $I_0$ which is a measurement in the absence of any NF (a blank). The premeasurement phase also includes the calibration of the NF sensor with standard NF concentrations.

The measurement phase includes sequentially:
the incubation of the NF sensor with the liquid sample, preferably a human serum sample, to be tested. This incubation phase is between about 5 min to about 1 hour, preferably between about 10 min to about 50 min, more preferably between about 20 min to about 40 min, even more preferably about 30 min. This incubation phase may be performed at a temperature ranging from about 10° C. to about 50° C., preferably from about 15° C. to about 35° C., more preferably from about 20° C. to about 25° C., even more preferably at a temperature of about 25° C. This step allows to charge the NF-MIP layer of the sensor in NF, proportionally to the NF concentration.
the washing of the sensor, preferably twice. The sensor can be washed in a PBS solution. The washing can be under agitation, preferably by vortexing at a speed ranging from about 400 rpm to 800 rpm, preferably at a speed of about 600 rpm, for about 2 min to about 10 min, preferably for about 5 min. This step allows to remove the non-NF molecules of the sample that are weakly bound to the NF-MIP layer as well the NF molecules that are not bound to the imprints.

the measurement of the NF concentration is performed by DPV after immersing the NF sensor into a KCl solution, preferably at 1 M, comprising a redox probe, preferably $K_3[Fe(CN)_6]/K_4[Fe(CN)_6]$, preferably at a 4 mM concentration. For example, DPV curves can be recorded in the range of potentials from 0 V to 0.4 V vs Ag/AgCl, with a pulse amplitude of 0.025 V, a pulse width of 0.05 s, and a step potential of 0.001 V.

Before the incubation of the sensor in the liquid sample to be tested, the liquid sample can be diluted so as the concentration of NF in the diluted solution is in the range of about 0.01 ng/ml to about 0.5 ng/ml, preferably in the range of about 0.06 ng/ml to about 0.2 ng/ml. For instance, human serum should be diluted between about 40 and about 60 times, preferably between about 45 and about 55 times, more preferably the human serum should be diluted about 50 times. In such a diluted human serum, the final concentration of BDNF should be between about 0.05 ng/ml and 0.2 ng/ml, preferably the final concentration of BDNF should be of about 0.11 ng/ml.

In a particular embodiment, the detection and/or measurement of the concentration of NF above mentioned further comprises a regeneration phase of the NF sensor. The regeneration phase of the sensor comprises the immersion, preferably twice, in a PBS solution under agitation. The PBS solution for the regeneration phase might comprise other chemicals such as a polysorbate (e.g. polysorbate 20), SDS, NaCl, HCl, acetic acid, derivatives or mixtures thereof. Preferably, the agitation is done at a speed ranging from about 800 rpm to 2000 rpm, preferably at a speed of about 1200 rpm, for about 2 min to about 10 min, preferably for about 5 min. The agitation can be induced by a vortex or any similar device well known from the man skilled in the art. This phase allows to unbind the NF molecules present in the imprints and to reuse the NF sensor. Preferably, the washed NF sensor is dried prior reusing. In a preferred embodiment, the NF sensor is regenerated between 1 and about 10 times, preferably between 1 and 5 times, more preferably between 1 and 3 times. In a most preferred embodiment, the NF Sensor is regenerated only 1 time.

Preferably, a new NF sensor is used for each measurement.

Still preferably, the detection and/or measurement of the concentration of NF above mentioned further comprise a data processing phase. The raw data obtained from the measurement phase, i.e. DPV current peak, can be normalized to the $I_0$ measured in the premeasurement phase. It can be calculated according to the following formula:

$$\ln=(I0-Ic)/I0$$

where, I0 is DPV current peak measured after the incubation of the SPE in a blank solution, Ic is the DPV current peak measured after incubation of the SPE in the liquid medium to be tested (i.e. a solution containing a particular concentration of sulfonamide).

In a particular embodiment, the NF SPE is used with a NIP SPE for comparison purpose. A NIP SPE is a SPE prepared with the same method as the method for preparing a NF SPE except that either the polymer layer coating the electrically conductive surface of the working electrode is not imprinted by a NF or that the NF molecules are not removed from the MIP layer, preferably the NF molecules are not removed from the MIP layer.

In a fourteenth aspect, the invention also relates to the use of a NF sensor for detecting and/or measuring the concentration of a NF in a liquid medium. Preferably the NF is BDNF. Preferably, the NF sensor is a NF SPE.

In a preferred embodiment, the invention relates to the use of a BDNF SPE for detecting BDNF or for measuring the concentration of BDNF in a liquid medium.

The NF and the BDNF are as described in the first aspect of the invention above mentioned. The NF sensor, the NF SPE and the BDNF SPE are as described in the fourth aspect of the invention above mentioned. The liquid medium is as described in the thirteenth aspect of the invention above mentioned.

In a fifteenth aspect, the invention also relates to an in-vitro diagnosis method, prognosis method, or method for assessing the effectiveness of a treatment of a disorder in which the concentration of a NF is impaired in a patient in needs thereof, wherein the concentration of an NF is measured in a sample from said patient according to the above mentioned in-vitro method of detection of a NF or of measuring the concentration of a NF. Preferably the NF is BDNF. Preferably, the NF sensor is a NF SPE.

In a preferred embodiment, the invention relates to an in-vitro diagnosis method, prognosis method, or method for assessing the effectiveness of a treatment of a disorder in which the concentration of a NF is impaired, wherein the presence or concentration of BDNF is detected or measured in a sample from said patient according to the above mentioned in-vitro method of detection of BDNF or of measuring the concentration of BDNF.

In a sixteenth aspect, the invention still relates to an in-vitro diagnosis method, prognosis method, or method for assessing the effectiveness of a treatment of a disorder selected from the group consisting of neurological disorders, mental disorders, neurodegeneration disorders, and metabolic disorders in a patient in need thereof, wherein the presence or concentration of an NF is detected or measured in a sample from said patient according to the above mentioned in-vitro method of detection of a NF or of measuring the concentration of a NF. Preferably the NF is BDNF. Preferably, the NF sensor is a NF SPE.

In a preferred embodiment, the invention relates to an in-vitro diagnosis method of a disorder selected from the group consisting of neurological disorders, mental disorders, neurodegeneration disorders, and metabolic disorders in a patient in needs thereof, wherein the presence or concentration of an NF is detected or measured in a sample from said patient according to the above mentioned in-vitro method of detection of a NF or of measuring the concentration of a NF. Preferably the NF is BDNF. Preferably, the NF sensor is a NF SPE. More preferably, the invention relates to an in-vitro diagnosis method of a disorder selected from the group consisting of neurological disorders, mental disorders, neurodegeneration disorders, and metabolic disorders in a patient in needs thereof, wherein the presence or concentration of BDNF is detected or measured in a sample from said patient according to the above mentioned in-vitro method of detection of BDNF or of measuring the concentration of BDNF.

In another preferred embodiment, the invention relates to an in-vitro prognosis method of a disorder selected from the group consisting of neurological disorders, mental disorders, neurodegeneration disorders, and metabolic disorders in a patient in needs thereof, wherein the presence or concentration of an NF is detected or measured in a sample from said patient according to the above mentioned in-vitro method of detection of a NF or of measuring the concentration of a NF. Preferably the NF is BDNF. Preferably, the NF sensor is a NF SPE. More preferably, the invention relates to an in-vitro prognosis method of a disorder selected from the group consisting of neurological disorders, mental disorders, neurodegeneration disorders, or metabolic disorders in a patient in needs thereof, wherein the presence or concentration of BDNF is detected or measured in a sample from said patient according to the above mentioned in-vitro method of detection of BDNF or of measuring the concentration of BDNF.

In a particular embodiment, the in-vitro prognosis method is for early-onset prognosis.

In still another preferred embodiment, the invention relates to an in-vitro method for assessing the effectiveness of a treatment of a disorder selected from the group consisting of neurological disorders, mental disorders, neurodegeneration disorders, and metabolic disorders in a patient in needs thereof, wherein the presence or concentration of an NF is detected or measured in a sample from said patient according to the above mentioned in-vitro method of detection of a NF or of measuring the concentration of a NF. More preferably, the invention relates to an in-vitro method for assessing the effectiveness of a treatment method of a disorder selected from the group consisting of neurological disorders, mental disorders, neurodegeneration disorders, or metabolic disorders in a patient in needs thereof, wherein the presence or concentration of BDNF is detected or measured in a sample from said patient according to the above mentioned in-vitro method of detection of BDNF or of measuring the concentration of BDNF.

The NF and the BDNF are as described in the first aspect of the invention above mentioned. The patient and the sample from the patient are as described in the thirtieth aspect of the invention above mentioned.

As used herein, the term "disorder in which the concentration of a NF is impaired" refers to a disorder in which the concentration of NF is significantly above or below its normal concentration, i.e. at least about 5%, 10%, 15%, 20%, 25%, 30%, 40%, 45%, 50% above or below its normal concentration.

As used herein, the term "neurological disorder" refers to any disorder of the nervous system and includes brain damages such as frontal lobe damage, parietal lobe damage, temporal lobe damage, and occipital lobe damage; brain dysfunction such as aphasia, dysgraphia, dysarthria, apraxia, agnosia, and amnesia; spinal cord disorders; peripheral neuropathy and other peripheral nervous system disorders; cranial nerve disorder such as trigeminal neuralgia; autonomic nervous system disorders such as dysautonomia; multiple system atrophy; seizure disorders such as epilepsy; movement disorders of the central and peripheral nervous system such as Parkinson's disease; essential tremor; amyotrophic lateral sclerosis; Tourette's Syndrome; multiple sclerosis and various types of peripheral neuropathy; sleep disorders such as narcolepsy; migraines and other types of headache such as cluster headache and tension headache; lower back and neck pain; central neuropathy; neuropsychiatric illnesses such as diseases and/or disorders with psychiatric features associated with known nervous system injury, underdevelopment, biochemical, anatomical, or electrical malfunction, and/or disease pathology e.g. attention deficit hyperactivity disorder, autism, obsessive compulsive disorder as well as the neurobehavioral associated symptoms of degeneration of the nervous system such as essential tremor, Huntington's disease, Alzheimer's disease, and organic psychosis, delirium and dementia, dizziness and vertigo, stupor and coma, head injury, stroke, tumors of the nervous system, multiple sclerosis and other demyelinating diseases, infections of the brain or spinal cord including meningitis, prion diseases, complex regional pain syndrome (a chronic pain condition), Rubinstein-Taybin, Rett syndrome and retinal degeneration.

As used herein, the terms "mental disorder", "mental illness" and "psychiatric disorder" are equivalent and refer to behavioral or mental pattern that causes significant distress or impairment of personal functioning including anxiety disorder such as phobias, generalized anxiety disorder, social anxiety disorder, panic disorder, agoraphobia, obsessive-compulsive disorder and post-traumatic stress disorder, mood disorders such as depression, major depression, and dysthymia, bipolar disorder, thought disorder, hallucinations, psychotic disorders such as schizophrenia, and delusional disorder, schizoaffective disorder, schizotypy, personality disorders such as paranoid, schizoid and schizotypal personality disorders, antisocial disorder, borderline disorder, histrionic disorder, narcissistic personality disorders, anxious-avoidant disorder, dependent disorder, obsessive-compulsive personality disorders, adjustment disorder, eating disorders such as anorexia nervosa, bulimia nervosa, exercise bulimia or binge eating disorder, sleep disorders such as insomnia, sexual disorders, gender dysphoria, impulse control disorders such as kleptomania or pyromania, behavioral addictions such as gambling addiction, substance use disorders such as substance dependence and substance abuse, dissociative identity disorders such as depersonalization disorder or dissociative Identity disorder, memory or cognitive disorders such as amnesia or various kinds of old age dementia, developmental disorders such as autism spectrum disorders, oppositional defiant disorder and conduct disorder, attention deficit hyperactivity disorder (ADHD), conduct disorders such as antisocial personality disorder, somatoform disorders such as somatization disorder and conversion disorder, body dysmorphic disorders, neurasthenia, and factitious disorders such as Munchausen syndrome.

As used herein, the terms "neurodegeneration disorder", "neurodegenerative disorder", "neurodegenerative diseases" and "degenerative nerve disease" are equivalent and refer to diseases in which occurs a progressive loss of structure or function of neurons, including death of neurons, and include Alzheimer's disease, amyotrophic lateral sclerosis, Friederichs's ataxia, Huntington's disease, Lewy body disease, Parkinson's disease, and Spinal muscular atrophy.

As used herein, the term "metabolic disorders" refers to disorders in which abnormal chemical reactions in the body alter normal the metabolic process and includes hypoxia, ischemia, and diabetes, obesity, metabolic syndrome, glaucoma, retinal degeneration.

The disorder according to the invention is selected from the group consisting of neurological disorders, mental disorders, neurodegeneration disorders, and metabolic disorders.

Preferably, the disorder according to the invention is selected from the group consisting in depressive disorders, schizophrenia, addiction disorder, bipolar disorders, anxiety-related disorders, post-traumatic stress disorder, Rett syndrome, Rubinstein-Taybi syndrome, eating disorders, Alzheimer's disease, Lewy body dementia, Huntington's disease, amyotrophic lateral sclerosis, epilepsy, Parkinson's disease, spinal cord injury, stroke, hypoxia, ischemia, brain injury, diabetes, peripheral neuropathy, chemotherapy induced neuropathy, nerve transplantation complications, multiple sclerosis, peripheral nerve injury, motor neuron disease, dementia, HIV dementia, hearing loss, obesity, metabolic syndrome, brain cancer, glaucoma, retinal degeneration, anesthesia-induced cognitive impairment, bipolar disorders, and autism.

More preferably, the disorder according to the invention is selective from the group consisting of depressive disorders, Alzheimer's disease, Parkinson's disease, Huntington's disease, and amyotrophic lateral sclerosis.

As used herein the term "diagnosis" refers to the detection and/or the identification in a patient of a disorder selected from the group consisting of neurological disorders, mental disorders, neurodegeneration disorders, and metabolic disorders.

As used herein the term "prognosis" refers to the prediction of the susceptibility of a patient to develop a disorder selected from the group consisting of neurological disorders, mental disorders, neurodegeneration disorders, and metabolic disorders, and/or to the prediction of the susceptibility of such a disorder to evolve to a further stage, and/or to the prediction of the issue of such a disorder.

As used herein, the term "treatment" refers to any treatment of a disease and/or disorder in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition, i.e., arresting its development; and (iii) relieving the disease, disorder and/or condition, i.e., causing regression of the disease, disorder and/or condition.

In a particular embodiment of the in-vitro method for diagnosis or prognosis or assessing the effectiveness of a treatment according to the invention, a concentration level in a sample, preferably a blood sample, more preferably a serum sample, from the patient superior to a certain threshold is indicative of a disorder, predictive of a disorder or indicative of the inefficiency of a treatment. Preferably, the threshold according to the invention is a threshold that has been determined for a specific NF, preferably BDNF, and eventually in relation to a specific disorder. For example, the threshold for BDNF can be about 20 ng/ml and about 150 ng/ml, such as about 40 ng/ml, about 50 ng/ml, about 60 ng/ml, about 100 ng/ml.

The subject invention also provides the following non-limiting embodiments:

1. A Molecularly Imprinted Polymer (MIP) layer coated electrically conductive surface, wherein said MIP layer comprises a m-phenylenediamine (m-PD) polymer and Neurotrophic Factor (NF) imprints;

2. A method for preparing a MIP layer coated electrically conductive surface, wherein the MIP layer comprises a m-PD polymer and NF imprints, and wherein the method comprises the following steps:
 1) formation of a cleavable linking layer on the electrically conductive surface;
 2) immobilization of NF molecules on the cleavable linking layer;
 3) polymerization of m-PD on the NF-immobilized electrically conductive surface thereby forming a polymeric layer coating said electrically conductive surface with entrapped NF; and
 4) cleavage of the cleavable linking layer thereby removing the NF molecules from the polymeric layer and obtaining the MIP layer;

3. The MIP layer coated electrically conductive surface according to embodiment 1 or the method for preparing a MIP layer coated electrically conductive surface according to embodiment 2, wherein the thickness of the MIP layer is between about 3.5 and about 7 nm, preferably the thickness of the MIP layer is of about 4.7 nm;

4. The method for preparing a MIP layer coated electrically conductive surface according to embodiment 2 or 3, wherein the formation of a cleavable linking layer according to step 1 comprises:
 1) the formation of a 4-aminothiophenol (4-ATP) monolayer on the electrically conductive surface; and
 2) the formation of a 3,3'-dithiobis(sulfosuccinimidyl propionate) (DTSSP) monolayer covalently linked to the 4-ATP monolayer;

5. The method for preparing a MIP layer coated electrically conductive surface according to anyone of embodiments 2 to 5, wherein the immobilization of NF molecules on the cleavable linking layer of step 2 comprises the immersion in a solution comprising between about 20 µg/ml and about 30 µg/ml, preferably about 25 µg/ml of NF;

6. The method for preparing a MIP layer coated electrically conductive surface according to anyone of embodiments 2 to 7, wherein the m-PD polymerization of step 3 is an electropolymerization, preferably comprising the steps of immersing the NF-immobilized electrically conductive surface in a solution comprising about 10 mM of m-PD and then applying to said NF-immobilized electrically conductive surface a constant potential of about 0.26 V until an electric charge of about 2 $mC/cm^2$ has been passed through the NF-immobilized electrically conductive surface;

7. A MIP layer coated electrically conductive surface directly obtained by the method according to anyone of embodiments 2 to 6;

8. A NF sensor comprising at least one MIP layer coated electrically conductive surface according to anyone of embodiments 1, 3, or 7;

9. The NF sensor according to embodiment 8, wherein the NF sensor is a Screen Printed Electrochemical sensor (SPE) and the at least one MIP layer coated electrically conductive surface is an electrically conductive surface of the working electrode of said SPE;

10. The use of a NF sensor according to embodiment 8 or 9 for detecting and/or measuring the concentration of a NF in a liquid medium;

11. An in-vitro method of detection of a NF in a liquid medium or of measuring the concentration of a NF in a liquid medium, the method comprising contacting a NF sensor according to embodiment 8 or 9 with said liquid medium;

12. The use according to embodiment 10, or the in-vitro method of detection of a NF or of measuring the concentration of a NF according to embodiment 11, wherein the liquid medium is a sample from a patient, preferably selected from blood samples, plasma samples, serum samples, lymph samples, urine samples, saliva samples, or cerebrospinal fluid samples, more preferably the sample from a patient is a serum sample;

13. An in-vitro diagnosis method, prognosis method or method for assessing the effectiveness of a treatment of a disorder selected from neurological disorders, mental disorders, neurodegeneration disorders, and metabolic disorders such as depressive disorders, Alzheimer's disease, Parkinson's disease, Huntington's disease, and amyotrophic lateral sclerosis in a patient in need thereof, wherein the presence or concentration of an NF is detected or measured in a sample from said patient according to the in-vitro method of detection of a NF or of measuring the concentration of a NF according to embodiment 11 or 12;

14. The use according to embodiment 12, the in-vitro method of detection of a NF or of measuring the concentration of a NF according to embodiment 12, or the in-vitro diagnosis method, prognosis method or method for assessing the effectiveness of a treatment according to embodiment 13, wherein the patient is a mammal, preferably a human; and 15. The MIP layer coated electrically conductive surface according to anyone of embodiments 1, 3, or 7, the method for preparing a MIP layer coated electrically conductive surface according to anyone of embodiments 2 to 6, the NF sensor according to embodiments 8 or 9, the use of a NF sensor according to anyone of embodiments 10, 12 or 14, the in-vitro method of detection of a NF or of measuring the concentration of a NF according to anyone of embodiments 11, 12 or 14, or the in-vitro diagnosis method, prognosis method or method for assessing the effectiveness of a treatment according to embodiment 13 or 14, wherein the NF is a neurotrophin, preferably selected from Brain Derived Neurotrophic Factor (BDNF), Nerve Growth Factor (NGF), neurotrophin 3 (NT3), neurotrophin 4 (NT4), and variants or combinations thereof, more preferably the NF is the BDNF.

Further aspects and advantages of this invention are disclosed in the following experimental section, which should be regarded as illustrative and not limiting the scope of this application.

Examples

The aim of these experiments was to develop a sensitive and specific MIP-SPE sensor for the detection of BDNF in a label-free fashion via differential pulse voltammetry.

The performances of MIP sensors are strictly dependent on the capability of interaction between the imprinted polymer and the specific used templating agent/analyte (i.e. BDNF here): such interaction varies in unpredictable manner depending on the chemical and physical characteristics of the respective molecules. The efficacy of such interaction determines the quality of the obtained mold, the ease in loading and unloading the analyte and, accordingly, the sensitivity, stability and reproducibility over time of the method of analysis. For example, an imprecise imprinting entails a reduced capability of binding to the target analyte and/or an increased interference caused by the binding of MIP with molecules different from the target. Therefore, the MIP sensors are always created "ad hoc", i. e. for the detection of a small and chemical-sterically homogeneous group of analytes and they require their own conditions of production process and measurement parameters, not a priori predictable or deducible from MIP sensors created for different analytes or based on different imprinted polymers. Critical parameters include, for example, the thickness of the produced polymer matrix, the conditions for removal of the templating agent after polymerization, the amount of imprinted templating agent, in particular the amount/accessibility of the binding sites obtained in the polymer matrix, the usage modes of the probe during measurement, the conditions of incubation with the target analyte (time, pH, etc.).

Material and Methods
Chemicals and Material

Acetic acid, 4-aminothiophenol (4-ATP), 2-mercaptoethanol, m-phenylenediamine (mPD), dimethyl sulfoxide (DMSO), human serum albumin (HSA), and sodium dodecyl sulfate (SDS) were purchased from Sigma-Aldrich. Human recombinant BDNF (13.5 kDa, pI 9.43), human recombinant Cerebral Dopamine Neurotrophic Factor (CDNF, 18.5 kDa, pI 7.68), human recombinant mesencephalic astrocyte-derived neurotrophic factor (MANF, 18.1 kDa, pI 8.55), and mouse recombinant mCD48 (cluster of differentiation 48, 22.2 kDa, pI 9.36) were provided by Icosagen AS (Tartu, Estonia). Ultrapure water (resistivity 18.2 MΩ·cm, Millipore, USA) was used for the preparation of all aqueous solutions. Phosphate buffered saline (PBS) solution (0.01 M, pH 7.4) was used to prepare analyte solutions. The screen-printed electrodes (SPE) were obtained from BVT Technologies AS (Praha, Czech Republic) (catalog #AC1.W1.R2).

BDNF-MIP Preparation

A BDNF-MIP layer was prepared on a SPE by electrochemical polymerization of m-phenylenediamine (m-PD) as a functional monomer in the presence of BDNF as a template. All stages of the preparation procedure are depicted in FIG. 1.

Firstly, the gold surface of a working electrode (WE) of a SPE was cleaned electrochemically in 0.1 M H2SO4 by applying cyclic voltammetry (potential range: 0.1 to 1.15 V, scan rate: 100 mV/s, number of cycles: 15).

Then, the cleaned gold surface of the WE was modified with amino groups by incubation in an ethanolic solution of 0.1 M of 4-aminothiophenol (4-ATP) for 1 h (FIG. 1A).

DTSSP (3,3'-dithiobis(sulfosuccinimidyl propionate)) was then covalently attached to the amino-functionalized surface of the working electrode of the SPE by immersion in a solution of 0.1 M PBS (at pH 7.4) containing 10 mM of DTSSP for 30 min (FIG. 1B).

BDNF was then immobilized on the DTSSP-functionalized surface of the SPE by applying a drop (2 µL) of a PBS buffer solution containing 25 µg/ml of BDNF for 30 min (FIG. 1C).

For the step of polymerization of m-PD, the BDNF-modified SPE was connected to an electrochemical workstation (Reference 600, Gamry Instruments, USA) and placed in a PBS solution containing 10 mM of m-PD. The electropolymerization of m-PD was conducted at a constant potential of 0.26 V (versus Ag/AgCl) applied to the WE until an electrical charge of 2 mC/cm$^2$ had been passed through the WE (FIG. 1D).

After the electropolymerization of m-PD, BDNF was removed from the polymer matrix by sequentially immersing the SPE in an ethanolic solution of 0.1 M of 2-mercaptoethanol overnight, which allows the destruction of the disulfide bonds present in the DTSSP molecules, and immersing the SPE in aqueous solution of 10% acetic acid for 30 min (FIG. 1E).

Finally, the SPE was washed with ultrapure water (18.2 MΩ·cm, 25° C.) and dried under nitrogen flow.

Figure 2A:
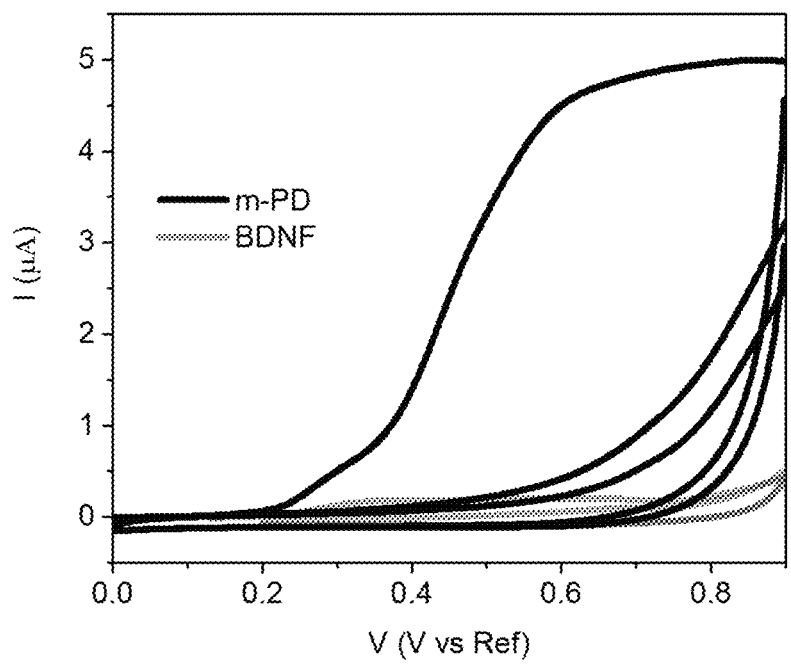
FIGS. 2A-2B: Optimization of the electrochemical polymerization. A: Cyclic voltammetry performed on a gold working electrode in PBS solution containing 10 mM m-PD or BDNF; B: The calibration graph representing the dependence of MIP film thicknesses on the amount of the charge applied during the electropolymerization of m-PD.

Electrochemical behavior of m-PD and BDNF in PBS solution was studied by Cyclic Voltammetry (CV). CV was performed by scanning potential between 0 and 0.7 V (versus Ag/AgCl) at a scan rate of 50 mV/s (FIG. 2A).

Figure 3:
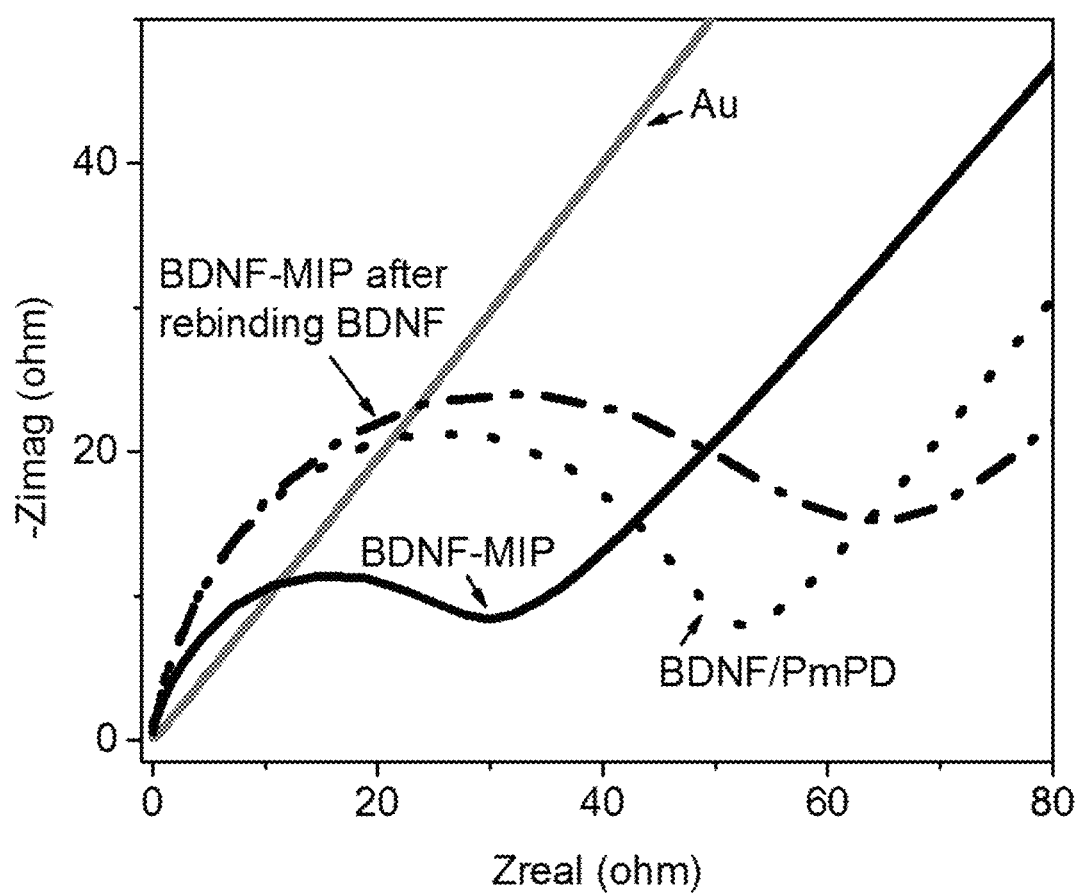
FIG. 3: Process of BDNF removal from the Poly m-PD layer. BDNF-MIP film formation. Nyquist plots performed in a 1 M KCl solution containing 4 mM of $K_3[Fe(CN)_6]$/$K_4[Fe(CN)_6]$ on (i) the bare gold, (ii) Poly-m-PD electrodeposited on BDNF immobilized on the bare gold via the cleavable linking layer, (iii) BDNF-MIP film formed after BDNF removal by linker cleavage and (iv) BDNF-MIP film incubated with 10 ng/ml BDNF solution in PBS.

The EIS spectra were recorded for frequencies from 100 kHz to 0.1 Hz at open circuit potential with an AC amplitude of 10 mV in a 1 M KCl solution containing 4 mM redox probe $K_3[Fe(CN)_6]/K_4[Fe(CN)_6]$ (FIG. 3).

The polymer film thicknesses were determined by spectroscopic ellipsometry (SE 850, Sentech Instruments GmbH, Berlin, Germany), measuring ellipsometric Psi and Delta spectra between 350 and 850 nm at 70° incidence angle in ambient air on three spots of each film.

Rebinding and Selectivity Study

Measurements of the binding affinity and selectivity of the BDNF-MIP-SPE toward the target (BDNF) were conducted by means of DPV. Before DPV measurements BDNF-MIP-SPE was incubated for 30 min in a solution with a specific concentration of BDNF (from 0.1 to 100 ng/ml of BDNF in PBS buffer). After that, unbound BDNF was removed by washing twice in PBS vortexed (600 rpm) for 5 min. Then DPV measurements were performed in a 1 M KCl solution containing 4 mM of a redox probe ($K_3[Fe(CN)_6]/K_4[Fe(CN)_6]$). The DPV curves were recorded in the potential range of 0 V to 0.4 V with pulse amplitude of 0.025 V, pulse width of 0.05 s and step potential of 0.001 V. The response signals of the BDNF-MIP-SPE was normalized DPV current peaks, B, calculated according to Eq (1):

$$B=(I_0-I_c)/I_0 \quad (1)$$

where, $I_0$ is the DPV current peak measured after incubation of the SPE in a blank PBS solution, $I_c$ is the DPV current peak measured after incubation of the SPE in a PBS solution containing a particular concentration (C) of BDNF.

The selectivity of the BDNF-MIP/SPE sensor was assessed by comparing the responses of the BDNF-MIP-SPE sensor towards BDNF with those of interfering proteins in the presence of 0.8 ng/ml human serum albumin (HSA, 67 kDa, pI 5.67). This concentration of HSA corresponds to the physiological norm of the content of HSA in human serum diluted 50-fold. Cerebral Dopamine Neurotrophic Factor (CDNF, 18 kDa, pI 7.68), mesencephalic astrocyte-derived neurotrophic factor (MANF, 18 kDa, pI 8.55) and mouse recombinant mCD48 antigen (Cluster of Differentiation 48, 22.3 kDa, pI 9.36) were chosen as interfering proteins.

Results

The choice of the monomer to use for polymerization was partially relying on computational modelling using molecular docking (MD) and quantum chemical calculation (QCC) combined approach as described elsewhere (Boroznjak, R. et al, Journal of Molecular Recognition, 2017, https://doi.org/10.1002/jmr.2635). Three electropolymerizable water soluble monomers: meta-phenylenediamine (m-PD), 3,4-ethylenedioxy-thiophene (EDOT) and dopamine (DOPA), were investigated as possible monomers for synthesis of BDNF-MIP films. The monomer capable of the formation of the more energetically stable non-covalent complex with BDNF should be preferred. According to the calculated results (Table 1 below) m-PD was selected as an optimal monomer for synthesis BDNF-MIP.

TABLE 1

The results of computational modelling for a monomer-BDNF complex.

| Monomer | MD, ΔGScore*, kJ/mol | QCC, ΣΔE**, kJ/mol |
|---|---|---|
| m-PD | 22.6 | 2121 |
| EDOT | 21.5 | 1699 |
| DOPA | 19.7 | 777 |

*ΔGScore is an empirical scoring function used by the MD software to score the energy-minimized poses in the ligand-protein complex.
**ΣΔE is the sum of H-bond interaction energies between monomer and accessible proton-acceptor groups of BDNF.

Furthermore, the electrochemical stability of BDNF at the potential ranges needed for m-PD polymerization was assessed (FIG. 2A). As it can be seen by the increase in anodic current, the oxidation of m-PD in PBS solution starts at ca 0.2 V while no current peaks are observed on the CV performed in PBS solution containing BDNF. This indicates that the BDNF is stable in the given potential range.

For synthesis of a protein-selective MIP film, it is essential to prevent the entrapment of proteins in the polymer matrix during the polymerization process. Therefore, in order to avoid overgrowing the polymer around the BDNF molecules, the thickness of the growing polymer film was controlled by amount of the electrical charge passed through the electrode.

Figure 2B:
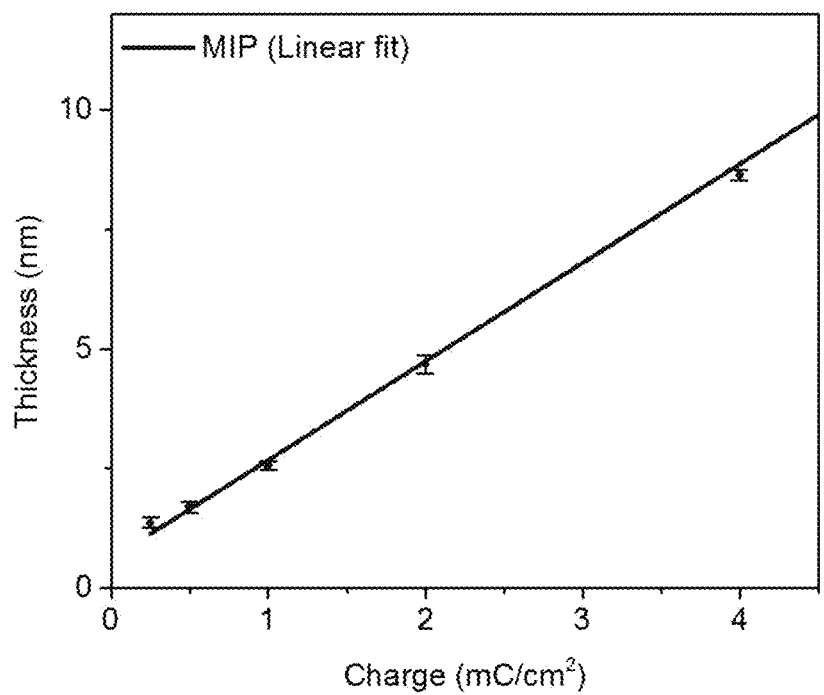

In order to find out the appropriate thicknesses for the polymer film, which confines, but does not irreversible entrap BDNF, the length of the whole immobilized structure containing the linker system and BDNF, was theoretically estimated. Assuming that the covalent attachment of BDNF via the succinimidyl group of DTSSP proceeds predominantly through its lysine residues that are abundant in the protein, the size of the resulting structure with random orientations of BDNF might vary from ca. 5.1 to 7.5 nm. Thus, the polymeric films having thickness not exceeding 5 nm were established to be optimal for the synthesis of BDNF-MIP. FIG. 2B shows the correlation between the amount of electrical charge applied during the in-situ electrodeposition of the polymer and the thicknesses of the resulting BDNF-MIP films. As it can be seen, the thicknesses of a BDNF-MIP varied linearly ($R^2=0.998$) across the applied electric charge range. The polymer film electrodeposited with the electrical charge 2 mC/cm$^2$ corresponding to the thickness of 4.8 nm was selected as an optimal for BDNF-MIP preparation.

To indirectly confirm the BDNF removal after the polymerization the EIS spectra were performed. As it can be seen in FIG. 3, the charge transfer resistance, estimated from the width of the semi-circle in the Nyquist plot, decreased after the procedure of cleavage the cleavable linking layer as compared to that of the Poly-m-PD with entrapped BDNF. The decrease in the charge transfer resistance is direct consequence of BDNF removal process facilitating further ability of the redox probe to transfer electrons to/from the surface of the Poly-mPD modified working electrode.

Figure 4A:
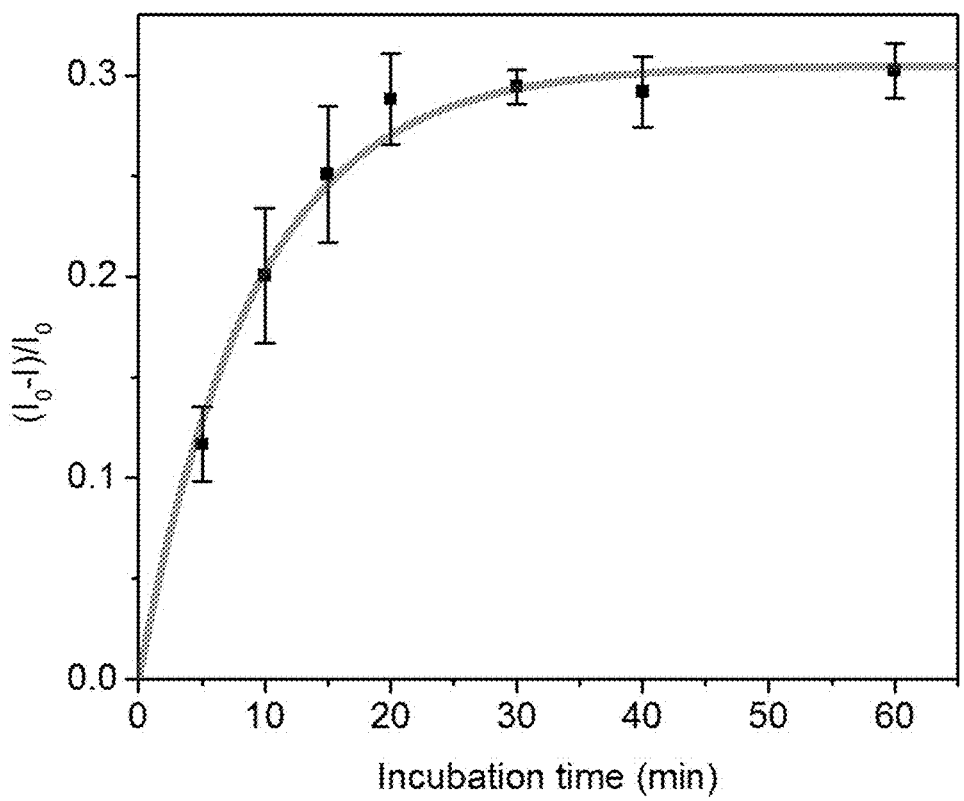
FIGS. 4A-4C: Rebinding study by Differential Pulse Voltammetry. A: The normalized response of BDNF-MIP/SPE sensor as a function of the incubation time in 5 ng/ml BDNF solution; B: Typical DPV curves recorded in a 1 M KCl solution containing 4 mM of $K_3[Fe(CN)_6]$/$K_4[Fe(CN)_6]$ on the BDNF-MIP modified SPE after incubation in solutions of different concentrations of BDNF in PBS buffer; C: The binding isotherms of BDNF to the BDNF-MIP-modified SPE and to the non-Imprinted Polymer (NIP) modified SPE. The NIP is Poly-m-PD electrodeposited on BDNF immobilized on the bare gold via the cleavable linking layer. The NIP is use as a reference film.

Firstly, in order to select the optimal binding conditions, the relationship between sensor signal B and the incubation time in the range of 5-60 min was studied. As it can be seen in FIG. 4A the sensor response increased rapidly within the first 20 min of incubation and reached saturation value after 30 min, indicating that the adsorption equilibrium was reached. Thus, the optimal incubation time of 30 min was chosen for the rebinding study.

Figure 4B:
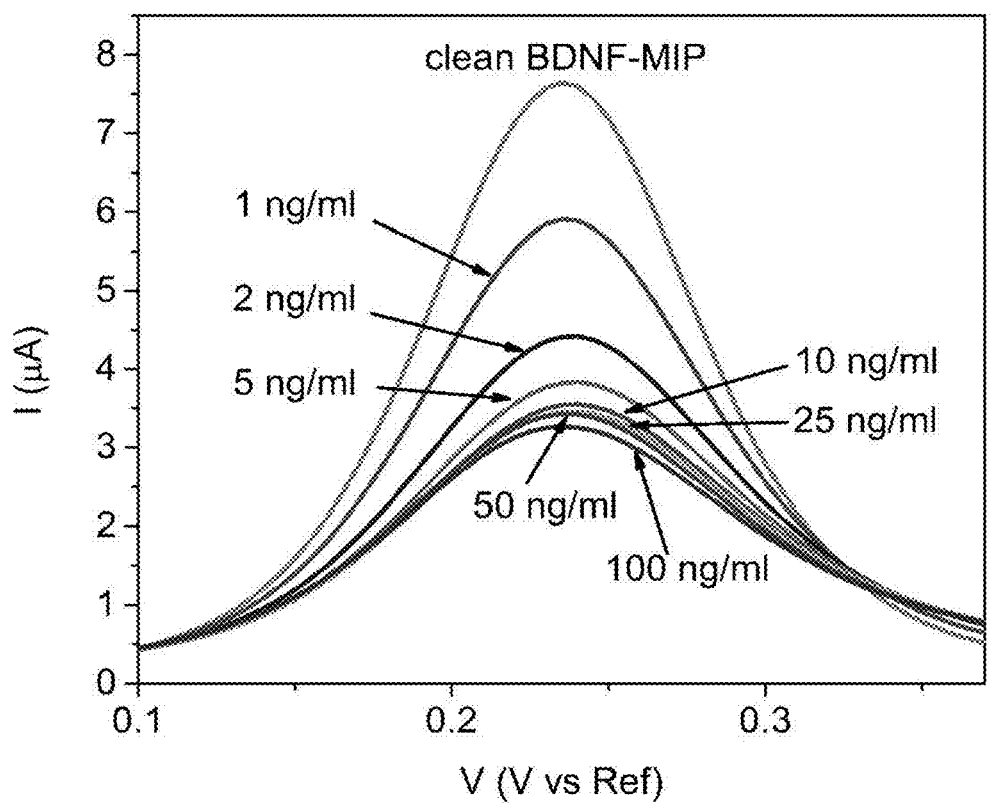

The binding affinity of the BDNF-MIP-SPE toward the target analyte BDNF were determined by means of DPV recorded after incubation of the sensor in the solution with increased concentration of analyte (FIG. 4B).

Figure 4C:
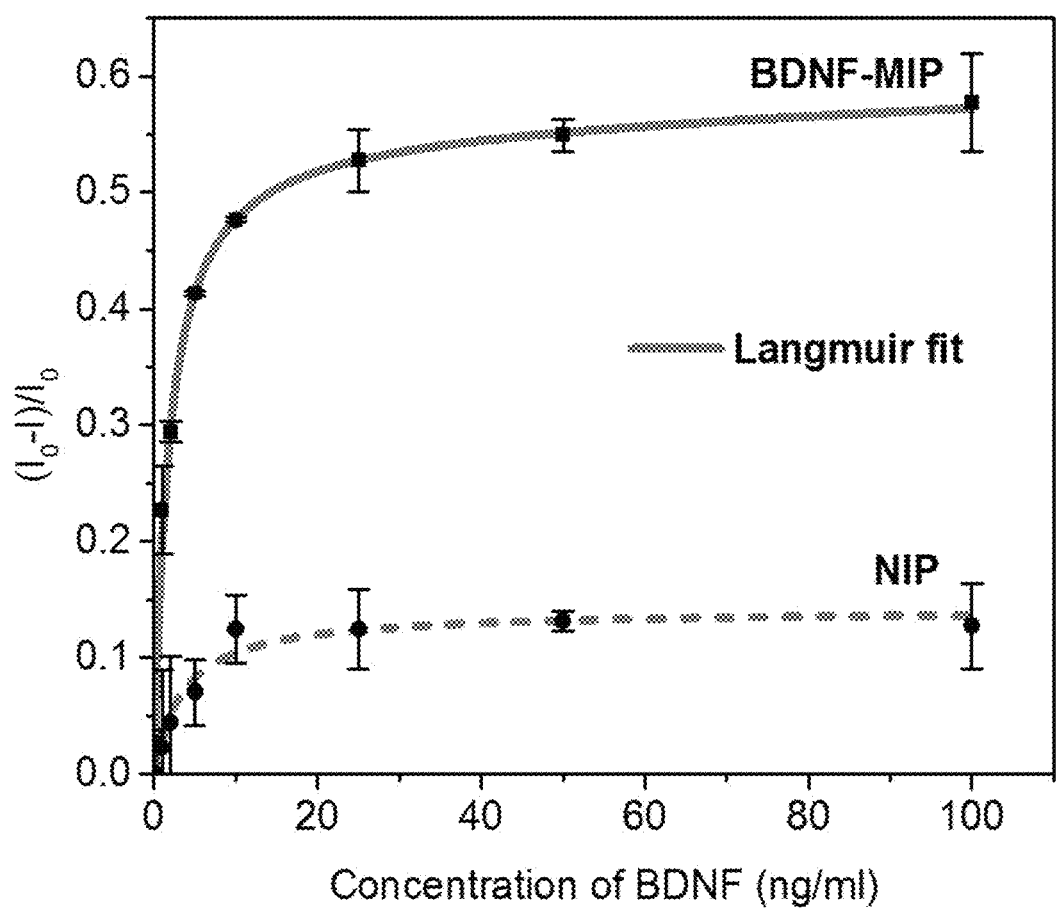

The B values calculated from Eq. (1) were used to plot the binding isotherm (FIG. 4C). The values of the dissociation constant ($K_D$) are derived from fitting the binding isotherms to Langmuir adsorption model (Eq. 2):

$$B=B_{max}C/(C+K_D) \quad (2)$$

where B and $B_{max}$ are the responses (Eq. 1) upon BDNF rebinding and saturation response, respectively, Cis BDNF concentration in PBS solution.

According to the model when all binding sites are occupied by molecules, further adsorption will not occur on the surface and saturation response ($B_{max}$) will be obtained. The fitting results showed that BDNF-MIP binds the target protein, BDNF, with dissociation constant Kd of 1.78±0.03 ng/ml, and has about 4 times higher binding capacity than NIP as judged by the respective $B_{max}$ values (0.56 vs 0.14).

Figure 5A:
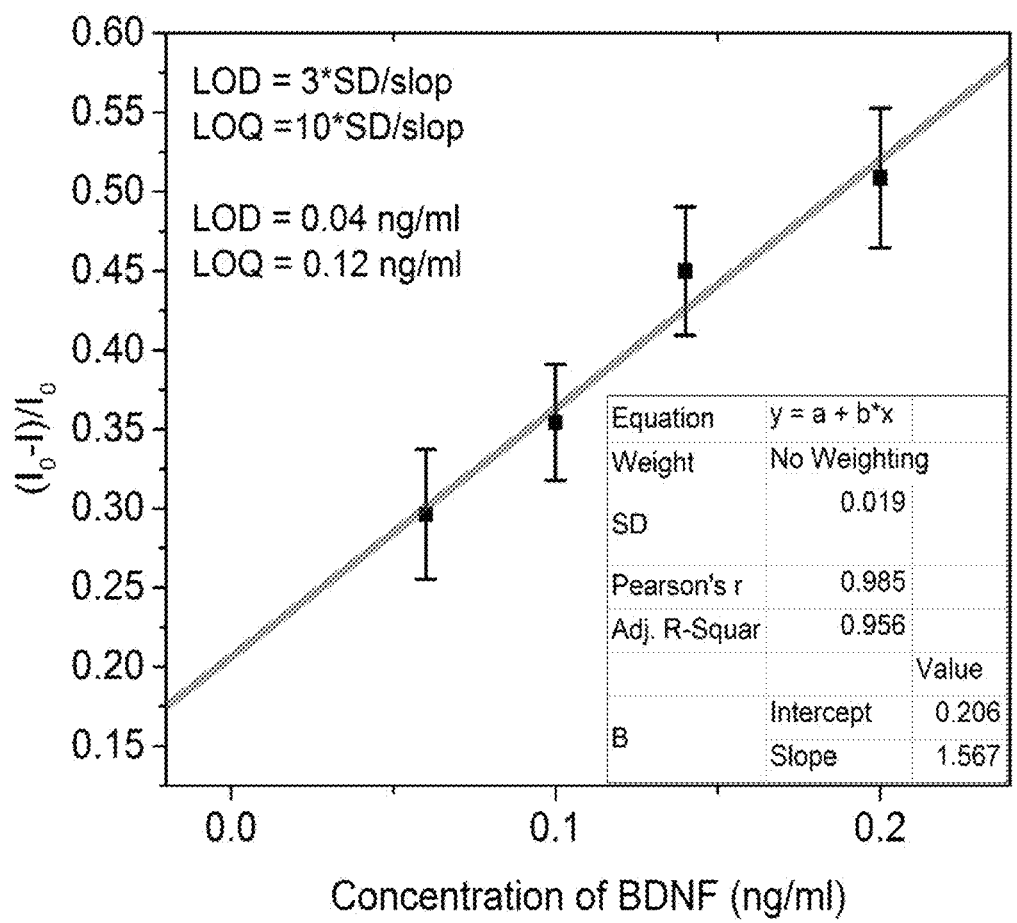
FIGS. 5A-5B: Limit of Detection (LOD), Limit of Quantitation (LOQ) and selectivity study. A: Determination of LOD and of the LOQ for BDNF-MIP-modified SPE sensors towards BDNF in the presence of 0.8 mg/ml HSA; B: The selectivity test of the BDNF-MIP-SPE towards BDNF, CDNF, CD48 and MANF conducted under noncompetitive conditions through incubation in PBS solutions having from 0.06 to 0.2 ng/ml of the respective interfering proteins in the presence of 0.8 mg/ml HSA.

The BDNF-MIP-SPE sensor shows a pseudo-linear response ($R^2=0.956$) to BDNF in the concentration range from 0.06 to 0.2 ng/ml and fixed concentration of 0.8 mg/ml of human serum albumin, HSA, the main plasma protein (FIG. 5A). The limit of detection (LOD) and limit of quantitation (LOQ), calculated as 3 and 10 times of the standard deviation (SD) divided by the slope of the regression line (Miller J. N. et al, Statistics and chemometrics for analytical chemistry, 6th ed2010, Harlow: Pearson Education Limited. 278 p.), equaled 0.04 ng/ml and 0.12 ng/ml, respectively.

Figure 5B:
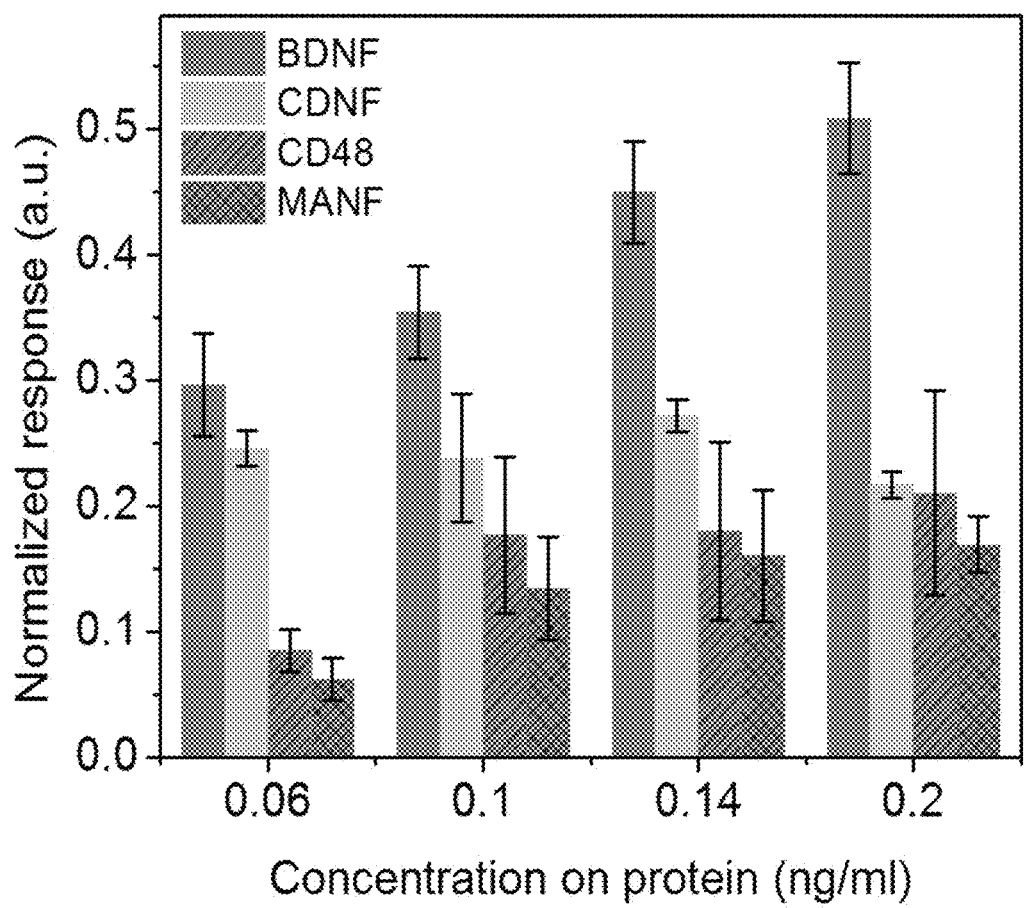

The selectivity of the BDNF-MIP-SPE was characterized in terms of its capability to rebind selectively the target protein, BDNF (27 kDa, Isoelectric point, pI, of 9.43), with respect to interfering proteins with slightly different size and pI: CDNF (18 kDa, pI 7.68), MANF (18 kDa, pI 8.55) and mCD48 (22.3 kDa, pI 9.36). The BDNF-MIP-SPE demonstrates more than 2 times higher response signal for target protein at concentration of 0.2 ng/ml than for any interfering proteins (FIG. 5B).

The present invention provides an accurate, inexpensive, direct and real-time transduction method to quantitatively evaluate the binding events of a target analyte (BDNF) at the relevant sensitivity levels.

BDNF-MIP-SPE was used for detection of BDNF in the concentration range of 0.01 ng/ml to 0.2 ng/ml in present of 0.8 mg/ml HSA, demonstrating sub-ng/mL LOD and LOQ. The BDNF-MIP-SPE is more selective to BDNF than to interfering proteins, such as CDNF, MANF and mCD48. Thus, the present invention is a fully functional electrochemical sensor for the detection of BDNF in liquid media. This invention can be spread to design similar sensors capable of detecting other proteins from the group of Neurotrophic Factors.

The invention claimed is:

1. A Molecularly Imprinted Polymer (MIP) layer coated electrically conductive surface, wherein said MIP layer comprises a m-phenylenediamine (m-PD) polymer and Neurotrophic Factor (NF) imprints.

2. A method for preparing a MIP layer coated electrically conductive surface, wherein the MIP layer comprises a m-PD polymer and NF imprints, and wherein the method comprises the following steps:
   1) formation of a cleavable linking layer on the electrically conductive surface;
   2) immobilization of NF molecules on the cleavable linking layer;
   3) polymerization of m-PD on the NF-immobilized electrically conductive surface thereby forming a polymeric layer coating said electrically conductive surface with entrapped NF; and
   4) cleavage of the cleavable linking layer thereby removing the NF molecules from the polymeric layer and obtaining the MIP layer.

3. The MIP layer coated electrically conductive surface according to claim 1, wherein the thickness of the MIP layer is between about 3.5 and about 7 nm.

4. The method for preparing a MIP layer coated electrically conductive surface according to claim 2, wherein the formation of a cleavable linking layer according to step 1 comprises:
   1) the formation of a 4-aminothiophenol (4-ATP) monolayer on the electrically conductive surface; and
   2) the formation of a 3,3'-dithiobis(sulfosuccinimidyl propionate) (DTSSP) monolayer covalently linked to the 4-ATP monolayer.

5. The method for preparing a MIP layer coated electrically conductive surface according to claim 2, wherein the immobilization of NF molecules on the cleavable linking layer of step 2 comprises the immersion in a solution comprising between about 20 µg/ml and about 30 µg/ml.

6. The method for preparing a MIP layer coated electrically conductive surface according to claim 2, wherein the m-PD polymerization of step 3 is an electropolymerization, preferably comprising the steps of immersing the NF-immobilized electrically conductive surface in a solution comprising about 10 mM of m-PD and then applying to said NF-immobilized electrically conductive surface a constant potential of about 0.26 V until an electric charge of about 2 mC/cm$^2$ has been passed through the NF-immobilized electrically conductive surface.

7. A MIP layer coated electrically conductive surface directly obtained by the method according to claim 2.

8. A NF sensor comprising at least one MIP layer coated electrically conductive surface according to claim 1.

9. The NF sensor according to claim 8, wherein the NF sensor is a Screen Printed Electrochemical sensor (SPE) and the at least one MIP layer coated electrically conductive surface is an electrically conductive surface of the working electrode of said SPE.

10. An in-vitro method of detection of a NF in a liquid medium or of measuring the concentration of a NF in a liquid medium, the method comprising contacting a NF sensor according to claim 8 with said liquid medium.

11. The in-vitro method of claim 10, wherein the liquid medium is a sample from a patient selected from blood samples, plasma samples, serum samples, lymph samples, urine samples, saliva samples, or cerebrospinal fluid samples.

12. An in-vitro diagnosis method, prognosis method or method for assessing the effectiveness of a treatment of a disorder selected from neurological disorders, mental disorders, neurodegeneration disorders, and metabolic disorders such as depressive disorders, Alzheimer's disease, Parkinson's disease, Huntington's disease, and amyotrophic lateral sclerosis in a patient in need thereof, wherein the presence or concentration of an NF is detected or measured in a sample from said patient according to the in-vitro method of detection of a NF or of measuring the concentration of a NF according to claim 10.

13. The method according to claim 11, wherein the patient is a mammal.

14. The MIP layer coated electrically conductive surface according to claim 1, wherein the NF is a neurotrophin.

15. The MIP layer coated electrically conductive surface according to claim 14, wherein the NF is selected from Brain Derived Neurotrophic Factor (BDNF), Nerve Growth Factor (NGF), neurotrophin 3 (NT3), neurotrophin 4 (NT4), and variants or combinations thereof.

16. The method according to claim 10, wherein the NF is a neurotrophin.

17. The method according to claim 16, wherein the NF is selected from Brain Derived Neurotrophic Factor (BDNF), Nerve Growth Factor (NGF), neurotrophin 3 (NT3), neurotrophin 4 (NT4), and variants or combinations thereof.

18. The method according to claim 12, wherein the NF is a neurotrophin.

19. The method according to claim 18, wherein the NF is selected from Brain Derived Neurotrophic Factor (BDNF), Nerve Growth Factor (NGF), neurotrophin 3 (NT3), neurotrophin 4 (NT4), and variants or combinations thereof.

* * * * *